(12) United States Patent
Speeg et al.

(10) Patent No.: US 8,529,465 B2
(45) Date of Patent: Sep. 10, 2013

(54) BIOPSY MARKER DELIVERY DEVICES AND METHODS

(75) Inventors: Trevor W. V. Speeg, Williamsburg, OH (US); Daniel J. Mumaw, Milford, OH (US); Kyle P. Moore, Mason, OH (US); Harold W. Craig, Cincinnati, OH (US); Frederick E. Shelton, IV, Hillsboro, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 233 days.

(21) Appl. No.: 12/862,816

(22) Filed: Aug. 25, 2010

(65) Prior Publication Data

US 2011/0071431 A1 Mar. 24, 2011

Related U.S. Application Data

(63) Continuation-in-part of application No. 12/565,968, filed on Sep. 24, 2009.

(51) Int. Cl.
*A61B 1/00* (2006.01)

(52) U.S. Cl.
USPC ............................ 600/562; 600/407; 600/568

(58) Field of Classification Search
USPC ................. 600/407, 423, 431–437, 562–572; 606/167, 170, 180
See application file for complete search history.

(56) References Cited

U.S. PATENT DOCUMENTS

| | | | | |
|---|---|---|---|---|
| 3,406,687 | A | * | 10/1968 | Moyer ........................... 604/117 |
| 4,402,308 | A | * | 9/1983 | Scott ................................. 600/7 |
| 5,526,822 | A | | 6/1996 | Burbank et al. |
| 6,086,544 | A | | 7/2000 | Hibner et al. |
| 6,228,055 | B1 | * | 5/2001 | Foerster et al. ................ 604/116 |
| 6,261,302 | B1 | * | 7/2001 | Voegele et al. ................ 606/151 |
| 6,347,241 | B2 | * | 2/2002 | Burbank et al. ............... 600/431 |
| 6,371,904 | B1 | | 4/2002 | Sirimanne et al. |
| 6,626,849 | B2 | | 9/2003 | Huitema et al. |
| 6,889,833 | B2 | | 5/2005 | Seiler et al. |
| 6,993,375 | B2 | | 1/2006 | Burbank et al. |
| 6,996,433 | B2 | | 2/2006 | Burbank et al. |
| 7,044,957 | B2 | | 5/2006 | Foerster et al. |
| 7,047,063 | B2 | | 5/2006 | Burbank et al. |
| 7,229,417 | B2 | | 6/2007 | Foerster et al. |
| 7,442,171 | B2 | | 10/2008 | Stephens et al. |
| 7,465,279 | B2 | | 12/2008 | Beckman et al. |

(Continued)

FOREIGN PATENT DOCUMENTS

EP 2156807 2/2010

OTHER PUBLICATIONS

U.S. Appl. No. 12/709,624, filed Feb. 22, 2010, Parihar.
U.S. Appl. No. 12/787,492, filed May 26, 2010, Speeg et al.

(Continued)

*Primary Examiner* — Rene Towa
(74) *Attorney, Agent, or Firm* — Frost Brown Todd LLC

(57) ABSTRACT

A biopsy system includes a biopsy device operable for taking one or more biopsy samples from a patient and a marker delivery device. The biopsy device includes a body portion having an alignment feature and a hollow biopsy needle extending distally from the body portion. The marker delivery device includes a marker deployer tube and an alignment feature associated with the marker deployer tube. The alignment feature on the marker delivery device is configured to matingly engage with the alignment feature on the biopsy device. A marker delivery device includes a resilient marker guide ramp.

20 Claims, 16 Drawing Sheets

(56) References Cited

U.S. PATENT DOCUMENTS

| | | |
|---|---|---|
| 7,507,210 B2 | 3/2009 | Hibner et al. |
| 7,693,567 B2 | 4/2010 | Tsonton et al. |
| 7,708,751 B2 | 5/2010 | Hughes et al. |
| 7,761,137 B2 | 7/2010 | Hardin et al. |
| 7,799,035 B2 | 9/2010 | Krueger et al. |
| 7,831,290 B2 | 11/2010 | Hughes et al. |
| 7,854,706 B2 | 12/2010 | Hibner |
| 7,862,517 B2 | 1/2011 | Tsonton et al. |
| 2004/0097981 A1* | 5/2004 | Selis .......................... 606/151 |
| 2006/0074345 A1 | 4/2006 | Hibner |
| 2006/0241385 A1 | 10/2006 | Dietz |
| 2006/0258956 A1 | 11/2006 | Haberstich et al. |
| 2007/0010738 A1 | 1/2007 | Mark et al. |
| 2007/0032742 A1 | 2/2007 | Monson et al. |
| 2007/0167736 A1 | 7/2007 | Dietz et al. |
| 2007/0255168 A1 | 11/2007 | Hibner et al. |
| 2008/0058672 A1 | 3/2008 | Shabaz et al. |
| 2008/0146962 A1 | 6/2008 | Ritchie et al. |
| 2008/0161720 A1 | 7/2008 | Nicoson et al. |
| 2008/0214955 A1 | 9/2008 | Speeg et al. |
| 2008/0221480 A1 | 9/2008 | Hibner et al. |
| 2009/0209853 A1 | 8/2009 | Parihar et al. |
| 2009/0209854 A1 | 8/2009 | Parihar et al. |
| 2009/0270725 A1 | 10/2009 | Leimbach et al. |
| 2010/0049084 A1 | 2/2010 | Nock et al. |
| 2010/0130887 A1 | 5/2010 | Selis |
| 2010/0152610 A1 | 6/2010 | Parihar et al. |
| 2010/0160819 A1 | 6/2010 | Parihar et al. |
| 2010/0160824 A1 | 6/2010 | Parihar et al. |
| 2010/0317997 A1 | 12/2010 | Hibner et al. |
| 2011/0071391 A1 | 3/2011 | Speeg |
| 2011/0071423 A1 | 3/2011 | Speeg et al. |

OTHER PUBLICATIONS

International Search Report and Written Opinion dated Dec. 27, 2010 for Application No. PCT/US2010/048737.

International Search Report and Written Opinion dated Mar. 12, 2012 for Application No. PCT/US2011/044323.

* cited by examiner

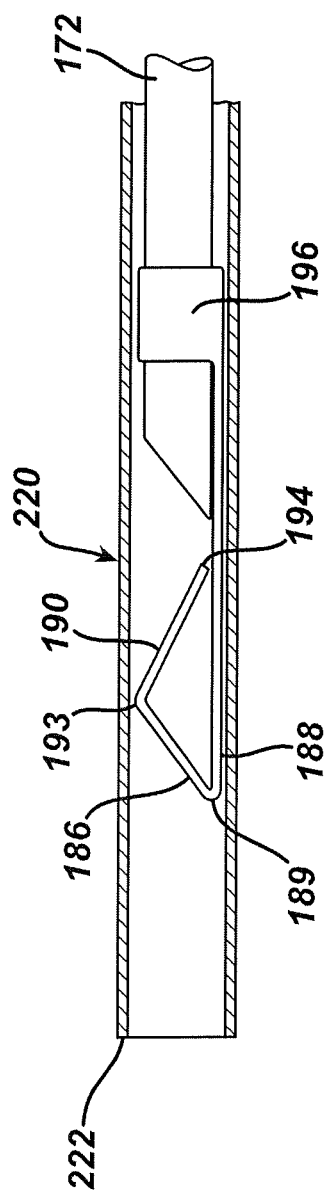
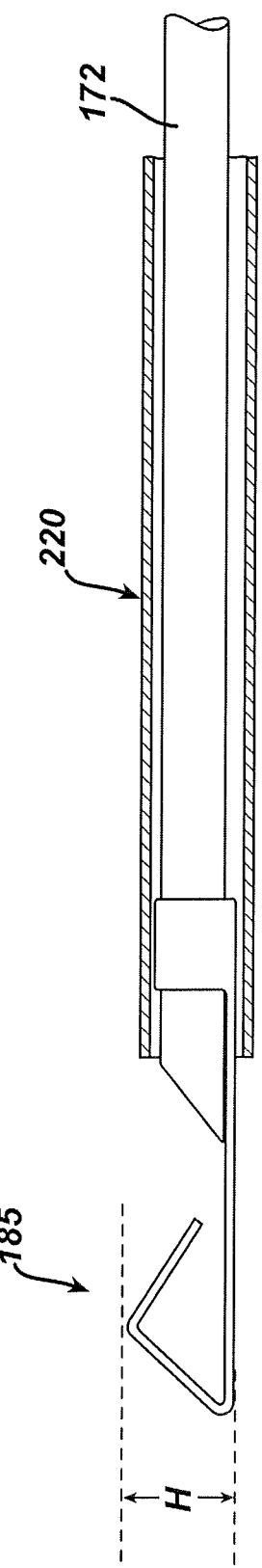

BIOPSY MARKER DELIVERY DEVICES AND METHODS

PRIORITY

This application is a continuation-in-part of application Ser. No. 12/565,968, entitled "Biopsy Marker Delivery Device with Positioning Component," filed Sep. 24, 2009.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. An exemplary biopsy device is the MAMMOTOME® brand device from Devicor Medical Products, Inc. of Cincinnati, Ohio.

Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; and U.S. Non-Provisional patent application Ser. No. 12/483,305, entitled "Tetherless Biopsy Device with Reusable Portion," filed Jun. 12, 2009. The disclosure of each of the above-cited U.S. Patents, U.S. Patent Application Publications, and U.S. Patent Applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Ethicon Endo-Surgery, Inc. of Cincinnati, Ohio. Further exemplary devices and methods for marking a biopsy site are disclosed in U.S. patent application Ser. No. 12/563,360, entitled "Flexible Biopsy Marker Delivery Device," filed Sep. 21, 2009; U.S. patent application Ser. No. 12/564,315, entitled "Biopsy Marker Delivery Device," filed Sep. 22, 2009; U.S. patent application Ser. No. 12/565,968, entitled "Biopsy Marker Delivery Device with Positioning Component," filed Sep. 24, 2009; U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. Patents, U.S. Patent Application Publications, and U.S. Patent Applications is incorporated by reference herein.

It may be desirable in some (but not necessarily all) settings to deploy markers through a biopsy device into the biopsy site, such as by using a flexible tubular deployer. In addition or in the alternative, it may be desirable to deploy markers through other types of cannulas.

While several structures and methods have been made and used for providing and using a marker applier device, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 17 depicts a partial cross-sectional view of the marker delivery device of FIG. 14 inserted in a cannula.

FIG. 18 depicts the same view as FIG. 17, with the marker delivery device advanced further distally in the cannula.

Figure 1:
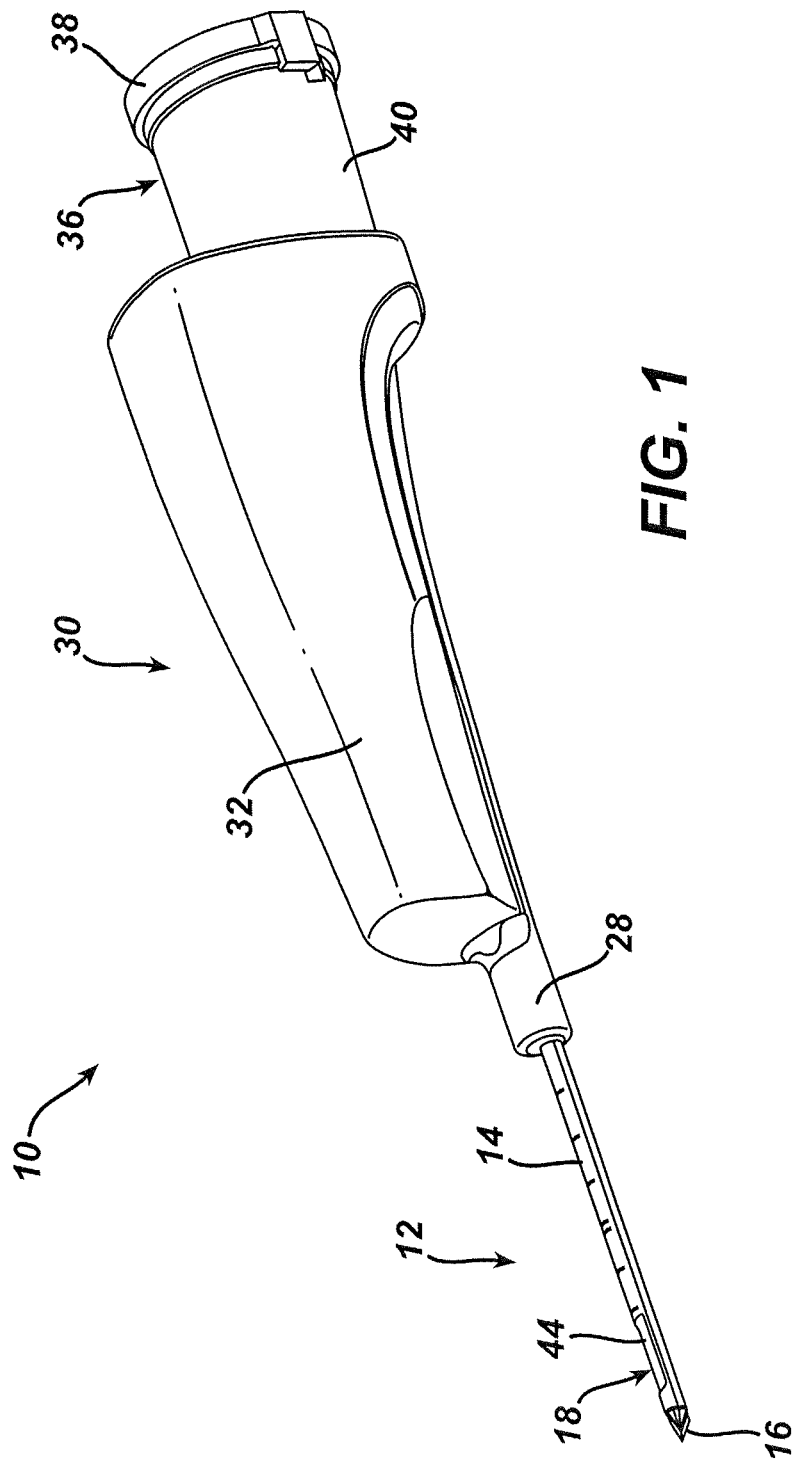
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Biopsy Device

FIGS. 1-6 illustrate an exemplary biopsy device (10). As shown in FIG. 1, biopsy device (10) comprises a needle (12), a body (30), and a cutter (44). In particular, needle (12) extends distally from the distal portion of body (30). Body (30) includes a housing (32) and a tissue sample holder (36) which extends proximally from the proximal portion of housing (32). Body (30) is sized and configured such that biopsy device (10) may be operated by a single hand of a user. In particular, a user may grasp housing (32), insert needle (12) into a patient's breast (or other location), and collect one or more tissue samples from within the patient's breast, all with just using a single hand. Alternatively, a user may grasp housing (32) with more than one hand and/or with any desired assistance. In some settings, the user may capture a plurality of tissue samples with just a single insertion of needle (12) into the patient's breast. Such tissue samples may be pneumatically deposited in tissue sample holder (36), and later retrieved from tissue sample holder (36) for analysis. While examples herein often refer to the acquisition of biopsy samples from a patient's breast, it should be understood that the exemplary biopsy devices described herein may be used in a variety of other procedures for a variety of other purposes and in a variety of other parts of a patient's anatomy.

Needle (12) of the present example comprises a cannula (14) with a tissue piercing tip (16), a lateral aperture (18), and a hub (28). Tissue piercing tip (16) is configured to pierce and penetrate tissue, without requiring a high amount of force, and without requiring an opening to be pre-formed in the tissue prior to insertion of tip (16). Alternatively, tip (16) may be blunt (e.g., rounded, flat, etc.) if desired. Lateral aperture (18) is configured to receive tissue from a tissue specimen location during operation of device (10). Cutter (44) is located within cannula (14). Cutter (44) rotates and translates relative to cannula (14) and past lateral aperture (18) to sever a tissue sample from tissue protruding through lateral aperture (18).

Hub (28) may be formed of plastic that is overmolded about needle (12) or otherwise secured to needle (12), such that hub (28) is unitarily secured to needle (12). Alternatively, hub (28) may be formed of any other suitable material through any suitable process and may have any other suitable relationship with needle (12). Hub (28) of the present example is coupled with a vacuum conduit (not shown), and is operable to communicate a vacuum (or atmospheric air, saline, pressurized fluid, etc.) from vacuum conduit to lateral aperture (18). Of course a vacuum may be communicated to lateral aperture (18) in any of a variety of other ways. The vacuum conduit may be coupled with a variety of sources, including but not limited to a vacuum source that is internal or external to biopsy device (10) in accordance with the teachings of U.S. Non-Provisional patent application Ser. No. 12/483,305, entitled "Tetherless Biopsy Device with Reusable Portion," filed Jun. 12, 2009, and/or U.S. Pub. No. 2008/0214955, entitled "Presentation of Biopsy Sample by Biopsy Device," published Sep. 4, 2008, the disclosures of which are incorporated by reference herein. Still other suitable fluid sources that a vacuum conduit may be coupled with will be apparent to those of ordinary skill in the art in view of the teachings herein. Of course, any suitable type of valve(s) and/or switching mechanism(s) may also be coupled with vacuum conduit, e.g., as taught in U.S. Non-Provisional patent application Ser. No. 12/483,305, entitled "Tetherless Biopsy Device with Reusable Portion," filed Jun. 12, 2009, and/or U.S. Pub. No. 2008/0214955, entitled "Presentation of Biopsy Sample by Biopsy Device," published Sep. 4, 2008, the disclosures of which are incorporated by reference herein. It should also be understood that a vacuum, atmospheric air, a liquid such as saline, etc. may also be selectively communicated to the lumen defined by cutter (44).

Body (30) of the present example comprises a housing (32) and tissue sample holder (36). In some versions, housing (32) is formed in at least two pieces, comprising a probe portion and a holster portion. For instance, in some such versions, the probe portion may be separable from the holster portion. Furthermore, the probe portion may be provided as a disposable component while the holster portion may be provided as a reusable portion. By way of example only, such a probe and holster configuration may be provided in accordance with the teachings of U.S. Non-Provisional patent application Ser. No. 12/483,305, entitled "Tetherless Biopsy Device with Reusable Portion," filed Jun. 12, 2009, and/or U.S. Pub. No. 2008/0214955, entitled "Presentation of Biopsy Sample by Biopsy Device," published Sep. 4, 2008, the disclosures of which are incorporated by reference herein. Alternatively, any other suitable probe and holster configuration may be used. It should also be understood that housing (32) may be configured such that it does not have a separable probe portion and holster portion. Various other suitable ways in which housing (32) may be configured will be apparent to those of ordinary skill in the art in view of the teachings herein.

Tissue sample holder (36) of the present example comprises a cap (38) and an outer cup (40). A filter tray (not shown) is provided within outer cup (40). Outer cup (40) is secured to housing (32) in the present example. Such engagement may be provided in any suitable fashion. Outer cup (40) of the present example is substantially transparent, allowing the user to view tissue samples on the filter tray, though outer cup (40) may have any other suitable properties if desired. The hollow interior of outer cup (40) is in fluid communication with cutter (44) and with a vacuum source in the present example. By way of example only, vacuum may be provided to outer cup (40), and such a vacuum may be further communicated to cutter (44), in accordance with the teachings of U.S. Non-Provisional patent application Ser. No. 12/483,305, entitled "Tetherless Biopsy Device with Reusable Portion," filed Jun. 12, 2009, and/or U.S. Pub. No. 2008/0214955, entitled "Presentation of Biopsy Sample by Biopsy Device," published Sep. 4, 2008, the disclosures of which are incorporated by reference herein. Various other suitable ways in which vacuum may be provided to outer cup (40) will be apparent to those of ordinary skill in the art in view of the teachings herein. It should also be understood that outer cup (40) may receive vacuum from the same vacuum source as the vacuum conduit in needle (12). Biopsy device (10) may further include one or more valves (e.g., shuttle valve, electromechanical solenoid valve, etc.) to selectively regulate communication of a vacuum and/or other fluids to outer cup (40) and/or vacuum conduit, regardless of whether outer cup (40) and vacuum conduit are coupled with a common source of vacuum or other source of fluid.

In the present example, when a tissue sample has been severed from a tissue specimen by cutter (44), the tissue sample is pulled from cutter (44) into tissue sampler holder (36) by the vacuum. As discussed further herein, in the present example outer cup (40) of tissue sample holder (36) is in fluid communication with the interior lumen of cutter (44) via a port extending through a distal portion of outer cup (40). Cap (38) is removably coupled with outer cup (40) in the present example such that a user may remove cap (38) to access tissue samples that have gathered on the filter tray (not shown) within outer cup (40) during a biopsy process. In addition, and as further described herein, cap (38) may be removed in order to allow the user to insert a marker delivery device into the interior lumen (48) of cutter (44) as well as the interior lumen (20) of cannula (14) in order to deploy a marker through lateral aperture (18) of cannula (14) into a patient. In some versions, a tissue receiving basket, filter, and/or other components are also removed from cup (40) before inserting the marker deliver device into cutter (44). Alternatively, cap (38) or the proximal end wall of tissue sample holder (36) may include an opening (or port) through which a marker delivery device may be inserted into the interior lumen of cutter (44) to deploy a marker through lateral aperture (18). A merely illustrative example of such an arrangement (an opening in the proximal end wall of the tissue sample holder) is shown in U.S. Pub. No. 2008/0214955, entitled "Presentation of Biopsy Sample by Biopsy Device," published Sep. 4, 2008, the disclosure of which is incorporated by reference herein.

In lieu of having a stationary filter tray, tissue sample holder (36) may have a plurality of trays that are removably coupled with a rotatable manifold, such that the manifold is operable to successively index each tray relative to cutter (44) to separately receive tissue samples obtained in successive cutting strokes of cutter (44). For instance, tissue sample holder (36) may be constructed and operable in accordance with the teachings of U.S. Pub. No. 2008/0214955, entitled "Presentation of Biopsy Sample by Biopsy Device," published Sep. 4, 2008, the disclosure of which is incorporated by reference herein. As another merely illustrative example, tissue sample holder (36) may be constructed and operable in accordance with the teachings of U.S. Pub. No. 2010/0160824, entitled "Biopsy Device with Discrete Tissue Chambers," published Jun. 24, 2010, the disclosure of which is incorporated by reference herein. Still other suitable ways in which tissue sample holder (36) may be constructed and operable will be apparent to those of ordinary skill in the art in view of the teachings herein.

It should be understood that, as with other components described herein, needle (12), body (30), housing (32), tissue sample holder (36), and cutter (44) may be varied, modified, substituted, or supplemented in a variety of ways, and that needle (12), body (30), housing (32), tissue sample holder (36), and cutter (44) may have a variety of alternative features, components, configurations, and functionalities. Several merely exemplary variations, modifications, substitutions, or supplementations are described in U.S. Non-Provisional patent application Ser. No. 12/709,624, entitled "Spring Loaded Biopsy Device," filed Feb. 22, 2010, the disclosure of which is hereby incorporated by reference. Still yet, other suitable alternative versions, features, components, configurations, and functionalities of needle (12), body (30), housing (32), tissue sample holder (36), and cutter (44) will be apparent to those of ordinary skill in the art in view of the teachings herein.

Figure 2:
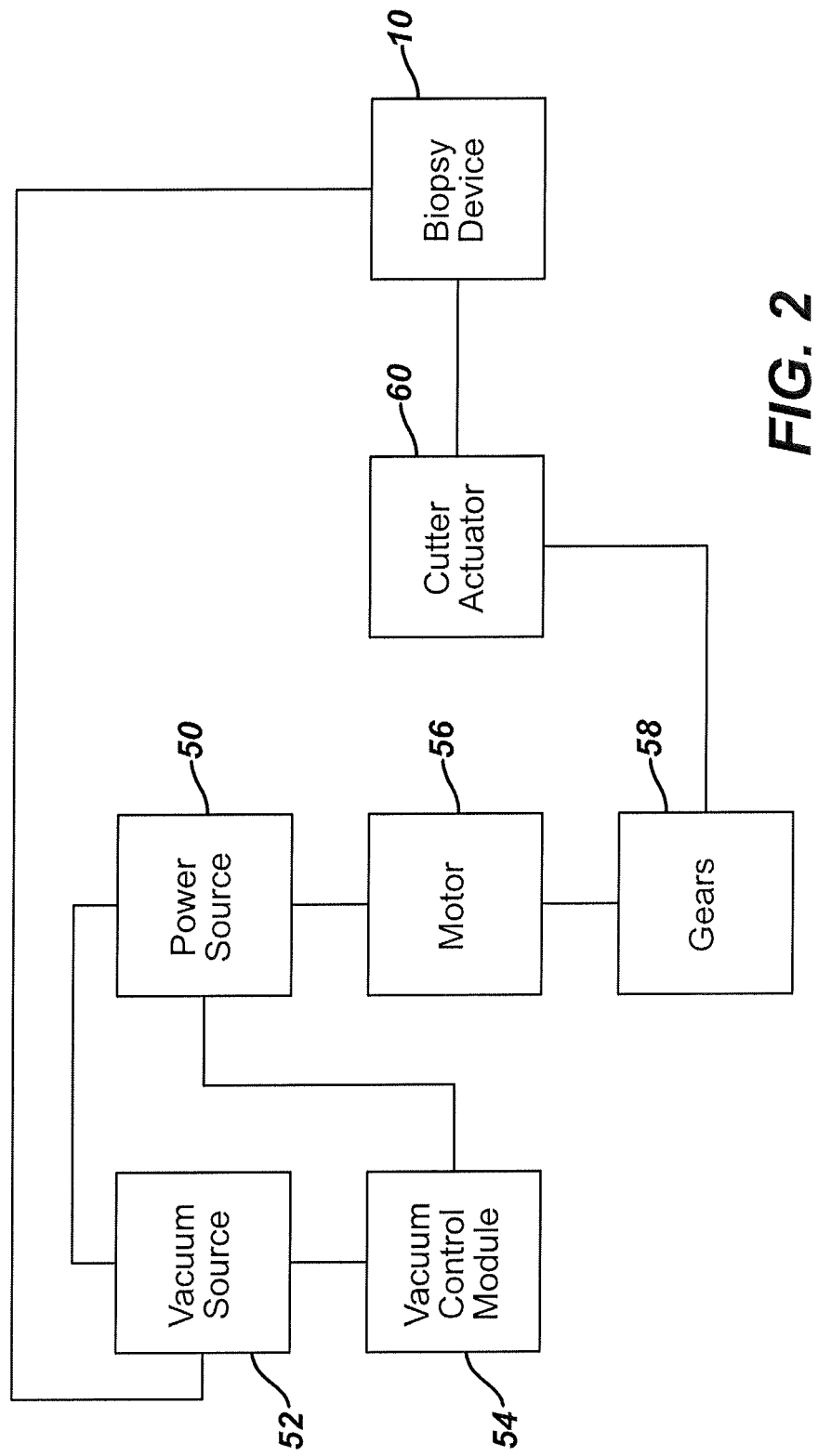
FIG. 2 depicts a block schematic view of components that are part of, or used with, the device of FIG. 1.

As shown in FIG. 2, exemplary components that are part of, or used with, the biopsy device (10) of FIG. 1, some of which have been introduced above, include a power source (50), a vacuum source (52), a vacuum control module (54), a motor (56), a set of gears (58), and a cutter actuator (60). In the present example, power source (50) provides power to vacuum source (52), vacuum control module (54), and motor (56). In some versions, power source (50) is located onboard biopsy device (10), e.g., a battery; while in some other versions, power source (50) is located some distance from biopsy device (10), e.g., line voltage from a standard electrical receptacle with a cable connection to biopsy device (10) and/or through an additional module between an electrical receptacle and biopsy device (10). Various configurations for and modifications to power source (50) will be apparent to those of ordinary skill in the art in view of the teachings herein.

In the present example, vacuum source (52) provides vacuum to biopsy device (10) for drawing tissue into lateral aperture (18) of needle (12). Vacuum source (52) also provides vacuum to biopsy device (10) for transporting a severed tissue sample from cutter (44) to tissue sample holder (36). In some versions, vacuum source (52) comprises a vacuum pump located onboard biopsy device (10). By way of example only, such an onboard vacuum source (52) may comprise a diaphragm pump that is driven by motor (56). In some such versions, vacuum source (52) is not coupled with power source (50) and vacuum control module (54) is omitted. In some other versions, vacuum source (52) comprises a vacuum pump located some distance from biopsy device (10) that provides vacuum via a vacuum cable or conduit. Of course, vacuum source (52) may comprise a combination of a vacuum pump located within housing (32) and a vacuum pump that is external to housing (32), if desired. In the present example, vacuum source (52) is in communication with vacuum control module (54). Vacuum control module (54) includes functions to control the supply and delivery of vacuum from vacuum source (52) to biopsy device (10). Various functions and capabilities that can be used with vacuum control module (54) to control how vacuum is supplied and delivered will be apparent to those of ordinary skill in the art in view of the teachings herein. Also, various other configurations for, and modifications to, vacuum source (52) and vacuum control module (54) will be apparent to those of ordinary skill in the art based on the teachings herein.

Motor (56) of the present example comprises a conventional DC motor, though it should be understood that any other suitable type of motor may be used. By way of example only, motor (56) may comprise a pneumatic motor (e.g., having an impeller, etc.) that is powered by pressurized air, a pneumatic linear actuator, an electromechanical linear actuator, a piezoelectric motor (e.g., for use in MRI settings), or a variety of other types of movement-inducing devices. As mentioned above, motor (56) receives power from power source (50). In some versions, motor (56) is located onboard biopsy device (10) (e.g., within housing (32)). In some other versions, motor (56) is located some distance from biopsy device (10) and provides energy to biopsy device (10) via a drive shaft or cable. In the present example, motor (56) is operable to rotate a drive shaft (not shown), which extends distally from motor (56) to gear set (58) to provide a rotary input into gear set (58). While the drive shaft extends directly from motor (56) into gear set (58), it should be understood that a variety of other components may be coupled between motor (56) and gear set (58), including but not limited to various gears, a clutch, etc. Gear set (58) includes an output shaft (not shown) having a drive gear (not shown) secured thereto, and is operable to selectively activate cutter actuator (60). Gear set (58) may comprise a planetary gearbox, and may be configured to provide speed reduction. Various suitable configurations for motor (56) and gear set (58) will be apparent to those of ordinary skill in the art in view of the teachings herein.

Cutter actuator (60) of the present example comprises a variety of components that interact to provide simultaneous rotation and distal translation of cutter (44) relative to body (30) and needle (12) in a firing stroke. Cutter actuator (60) is also operable to retract cutter (44) proximally to ready cutter (44) for firing. By way of example only, cutter actuator (60) may be configured and operable in accordance with the teachings of U.S. Non-Provisional patent application Ser. No. 12/709,624, entitled "Spring Loaded Biopsy Device," filed Feb. 22, 2010, and/or U.S. Pub. No. 2008/0214955, entitled "Presentation of Biopsy Sample by Biopsy Device," published Sep. 4, 2008, the disclosures of which are incorporated by reference herein. It should be understood that, as with other components described herein, cutter actuator (60) may be varied, modified, substituted, or supplemented in a variety of ways, and that cutter actuator (60) may have a variety of alternative features, components, configurations, and functionalities. Suitable alternative versions, features, components, configurations, and functionalities of cutter actuator (60) will be apparent to those of ordinary skill in the art in view of the teachings herein.

Figure 3:
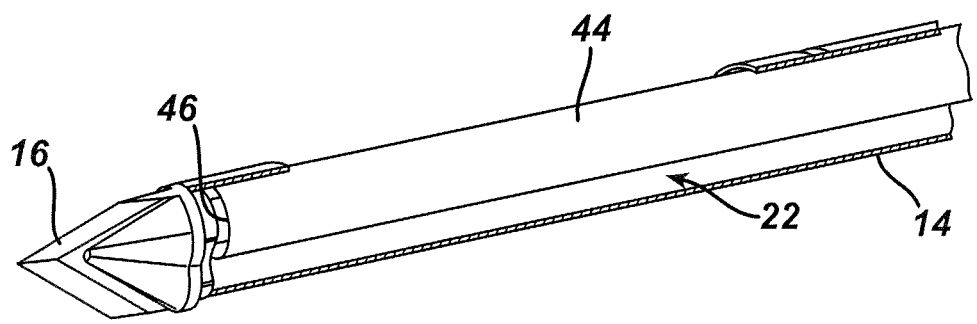
FIG. 3 depicts a first series view of part of the needle of the biopsy device of FIG. 1, with the needle shown in cross section and with the cutter in the initial, distal position.
Figure 4:
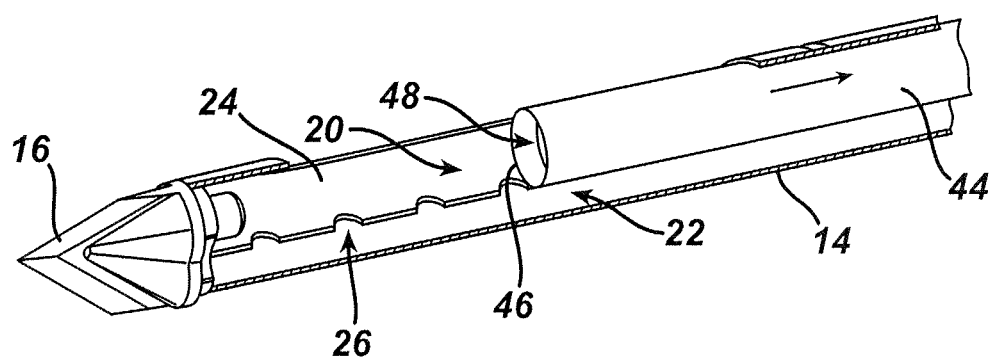
FIG. 4 depicts a second series view of part of the needle of the biopsy device of FIG. 1, with the needle shown in cross section and with the cutter in an intermediate position during retraction.
Figure 9:
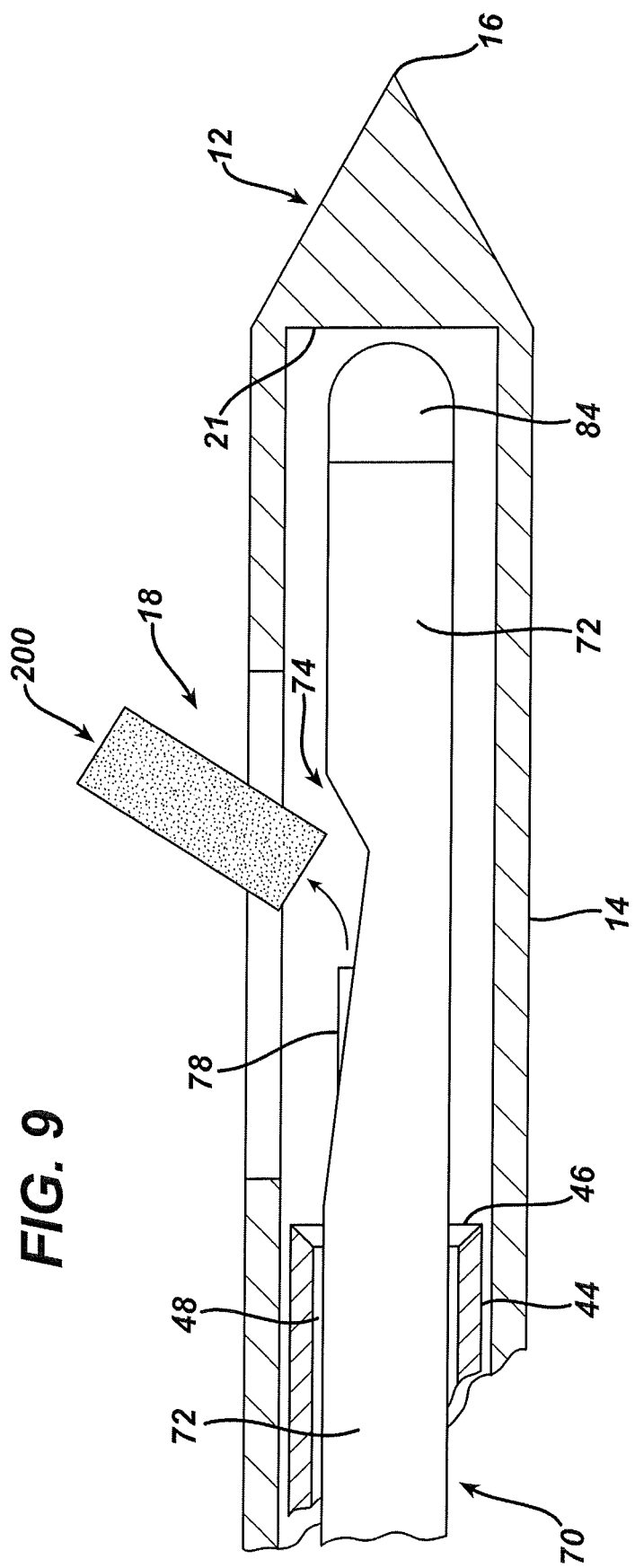
FIG. 9 depicts a side view the marker delivery device of FIG. 7 inserted in a biopsy device needle, with the biopsy device needle shown in cross-section, and with a marker being deployed through aligned lateral openings of the marker delivery device and the biopsy device needle.

As shown in the series views of FIGS. 3-6, an exemplary cutter (44) firing sequence is shown. FIG. 3 depicts cutter (44) in a distal position, with distal edge (46) of cutter (44) positioned distal of lateral aperture (18) thereby effectively "closing" lateral aperture (18) of needle (12). In this configuration, needle (12) can be inserted into a patient without tissue prolapsing through lateral aperture (18). FIG. 4 depicts cutter (44) being retracted by cutter actuator (60), thereby exposing tissue to lateral aperture (18) and revealing a cutter lumen (48) of cutter (44). In the present example, cutter (44) is positioned within a first lumen (20) of cannula (14). Beneath first lumen (20) is a second lumen (22), which is in part defined by a divider (24). Divider (24) comprises a plurality of openings (26) that provide fluid communication between first and second lumens (20, 22). Alternatively, and as depicted in FIG. 9, needle (12) may lack second lumen (22) altogether in some versions, such that first lumen (20) is the only lumen defined by needle (12).

A plurality of external openings (not shown) may also be formed in needle (12), and may be in fluid communication with second lumen (22). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Cutter (44) may also include one or more side openings (not shown). Of course, as with other components described herein, such external openings in needle (12) and cutter (44) are merely optional.

Figure 5:
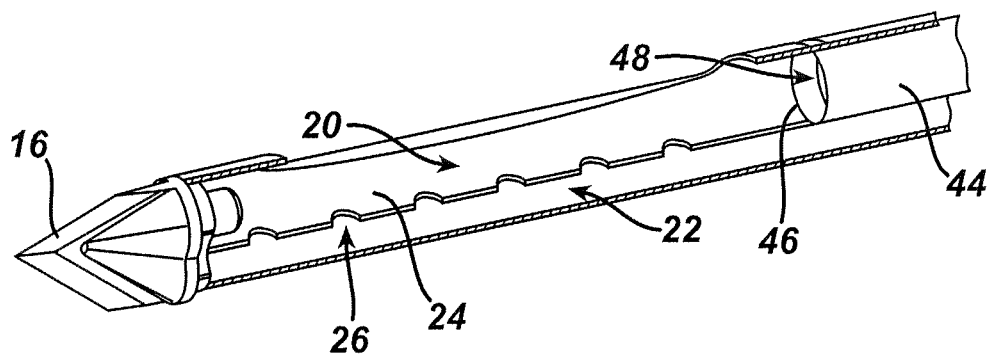
FIG. 5 depicts a third series view of part of the needle of the biopsy device of FIG. 1, with the needle shown in cross section and with the cutter in the retracted, proximal position.
Figure 6:
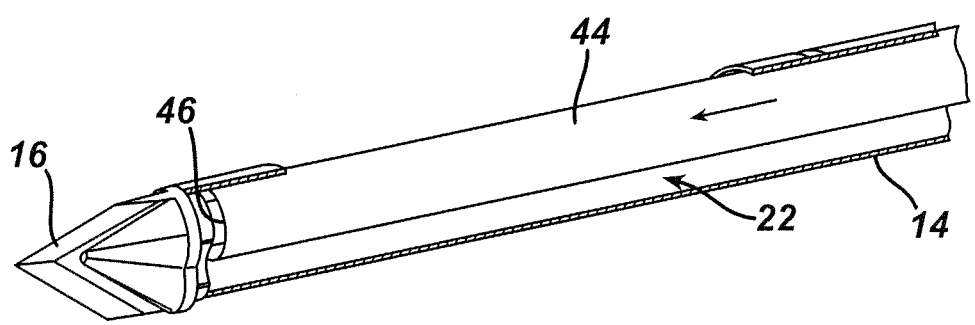
FIG. 6 depicts a fourth series view of part of the needle of the biopsy device of FIG. 1, with the needle shown in cross section and with the cutter in the advanced, distal position.
Figure 7:
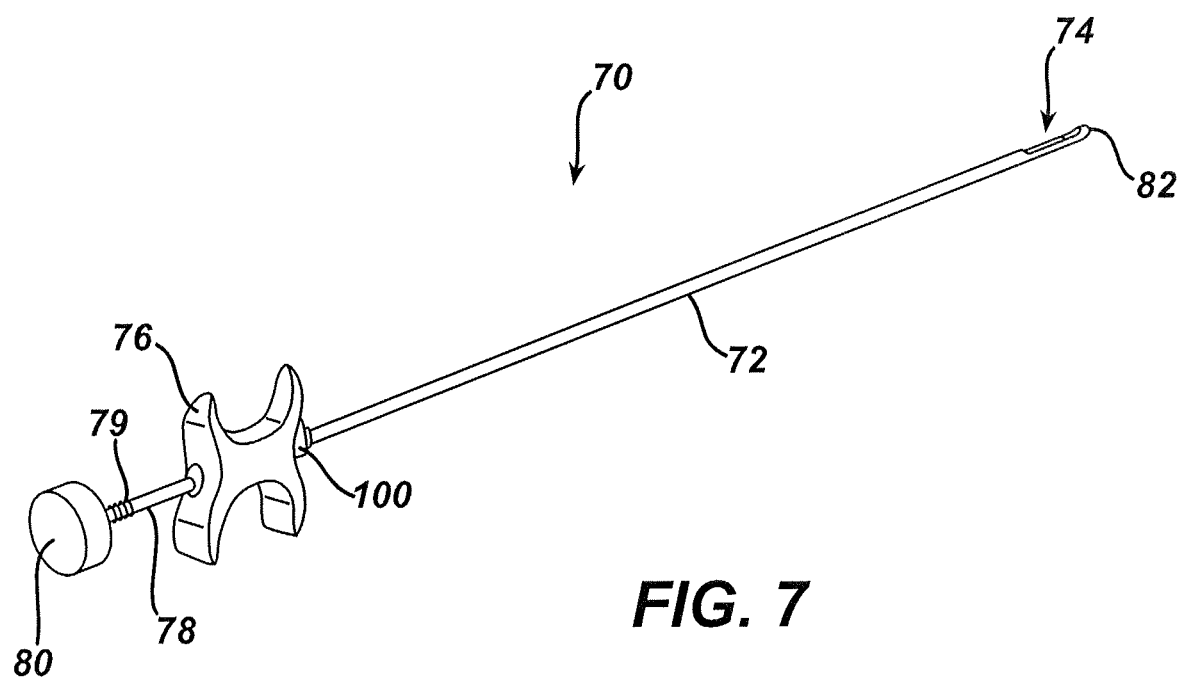
FIG. 7 depicts a perspective view of an exemplary marker delivery device.

FIG. 5 depicts cutter (44) fully retracted by cutter actuator (60), such that lateral aperture (18) is completely unobstructed by cutter (44). In this configuration tissue can prolapse through lateral aperture (18) within first lumen (20) under the force of gravity, due to internal pressure of the tissue (e.g., caused by displacement of the tissue upon insertion of needle (12), etc.), and/or with vacuum provided through second lumen (22) and transmitted through openings (26) and/or by vacuum provided through cutter lumen (48). FIG. 6 depicts cutter (44) after it has been advanced to close off lateral aperture (18) once tissue has been captured within first lumen (20), thereby severing the captured tissue. With the tissue severed, it is captured within cutter lumen (48) and ready for proximal transport to tissue sample holder (36). Such proximal transport of tissue through cutter lumen (48) to reach tissue sample holder (36) may be provided by drawing a vacuum through the proximal portion of cutter lumen (48) (e.g., behind the captured tissue sample) while venting a distal portion of cutter lumen (48) (e.g., in front of the captured tissue sample) to provide a pressure differential. Alternatively, tissue samples severed by cutter (44) may be communicated proximally to tissue sample holder (36), or be otherwise dealt with, in any other suitable fashion.

While the above paragraphs provide an enabling description of an exemplary biopsy device (10) and its use, further description as well as exemplary methods of operation are provided with the teachings of U.S. Non-Provisional patent application Ser. No. 12/709,624, entitled "Spring Loaded Biopsy Device," filed Feb. 22, 2010, U.S. Pub. No. 2008/0214955, entitled "Presentation of Biopsy Sample by Biopsy Device," published Sep. 4, 2008, and U.S. Non-Provisional patent application Ser. No. 12/483,305, entitled "Tetherless Biopsy Device with Reusable Portion," filed Jun. 12, 2009, the disclosures of which are incorporated by reference herein. Of course, the above examples of construction and use of biopsy device (10) are merely illustrative. Other suitable ways in which biopsy device (10) may be made and used will be apparent to those of ordinary skill in the art in view of the teachings herein.

II. Exemplary Marker Delivery Device

Following use of biopsy device (10), it may be desirable to mark the location of the biopsy site for future reference. In addition or in the alternative, it may be desirable to deploy one or more markers in a patient without first obtaining a tissue sample from the site to be marked. FIGS. 7-11 illustrate an exemplary marker delivery device (70) that may be used, for example, in conjunction with biopsy device (10) (e.g., such that biopsy device (10) and marker delivery device (70) together provide a biopsy system). Marker delivery device (70) may also be used with any of a variety of other biopsy devices, such as those having a laterally extending aperture through which tissue samples are acquired. In addition, marker delivery device (70) may be used with other types of cannulas.

Figure 8:
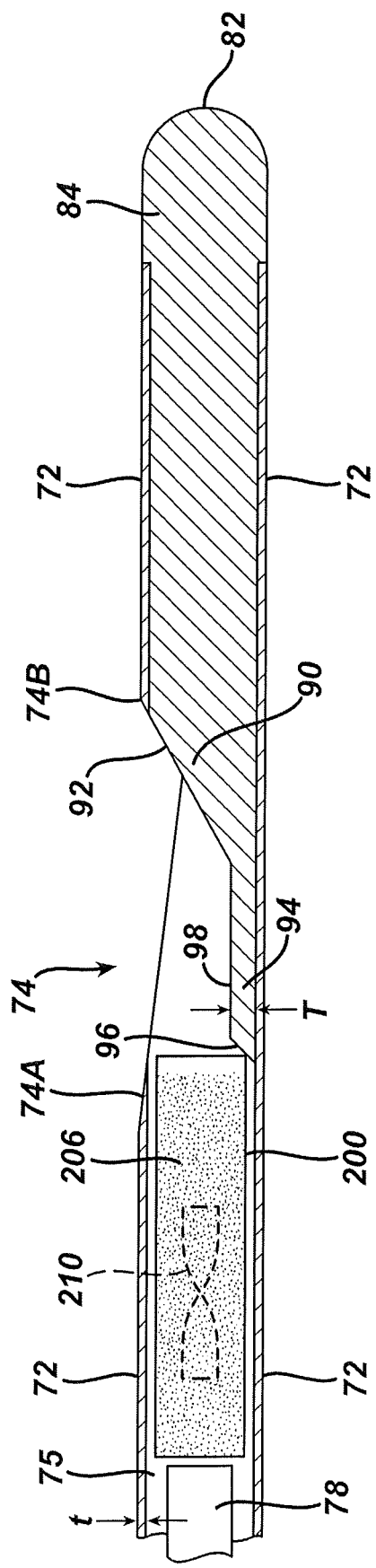
FIG. 8 depicts a cross-sectional view of a distal portion of the marker delivery device of FIG. 7.

Marker delivery device (70) of the present example includes an elongate, flexible deployer tube (72) having a side opening (74) formed near to, but spaced proximally from, the distal end of the deployer tube (72). A grip (76) is provided at the proximal end of deployer tube (72). A push rod (78) extends coaxially in deployer tube (72). Push rod (78) is configured to be translatable within deployer tube (72) to deploy one or more markers (200) through the side opening (74) as shown in FIGS. 8-9. Deployer tube (72) and push rod (78) may be relatively flexible in bending so that the deployer tube (72) may be inserted along a straight or curved path to deploy a marker element (200) at a biopsy site or other location within a patient. A plunger (80) is provided at the proximal end of rod (78) for pushing rod (78) distally in deployer tube (72) to deploy a marker (200) out of the deployer tube (72). A user may grasp grip (76) with two fingers, and may push on plunger (80) using the thumb on the same hand, so that marker delivery device (70) may be operated by a user's single hand. In the example shown, push rod (78) is biased proximally relative to grip (76) and deployer tube (72) by spring (79). Of course any of a variety of other features or structures may be used to bias push rod (78) in this manner, or such biasing may be omitted.

FIG. 8 depicts a cross-sectional view of a distal portion of marker delivery device (70). FIG. 8 shows a biopsy marker (200) disposed in the internal lumen (75) of deployer tube (72). Marker (200) of the present example comprises a biodegradable or otherwise bioresorbable body (206), such as a generally cylindrically shaped body of collagen or other suitable polymeric material, and a metallic, generally radiopaque marker element (210) (shown in phantom) disposed within or otherwise carried by the body (206). Marker (200) may be composed and/or configured in accordance with the teachings of any of the various U.S. Patents, U.S. Patent Application Publications, or U.S. Patent Applications cited herein. Alternatively, marker (200) may have any other suitable composition and/or configuration. It should also be understood that a plurality of markers (200) may be provided within deployer tube (72) (e.g., in an end-to-end arrangement, etc.), if desired. If a plurality of markers (200) are used, it should be understood that a plurality of markers (200) within a single deployer tube (72) may have the same size, shape, and/or composition. Alternatively, a plurality of markers (200) within a single deployer tube (72) may have different sizes, shapes, and/or compositions.

Deployer tube (72) may be formed of any suitable metallic or non-metallic material, or even a combination of metallic and non-metallic materials. In the present example, deployer tube (72) is a relatively flexible, thin-walled, hollow tube formed of a suitable medical grade plastic or polymer. One suitable material is a thermoplastic elastomer, such as Polyether block amide (PEBA), such as is known under the tradename PEBAX. Deployer tube (72) may thus be formed of PEBAX, and may be substantially transparent to visible light and X-ray. Side opening (74) may be formed by cutting away a portion of the wall of deployer tube (72), or using any other suitable technique. Side opening (74) communicates with the internal lumen (75) of deployer tube (72). Side opening (74) extends axially (in a direction parallel to the axis of lumen (75)) from a proximal opening end (74A) to a distal opening end (74B), as illustrated in FIG. 8.

The distal tip (82) extending from the distal end of deployer tube (72) may be rounded as shown in FIG. 8. Of course, distal tip (82) may alternatively have any other suitable configuration. Still referring to FIG. 8, marker delivery device (70) of the present example has the distal end of deployer tube (72) closed by a unitary endpiece (84) formed in place in the distal end of deployer tube (72), with a part of endpiece (84) extending into internal lumen (75) of deployer tube (72). Distal endpiece (84) may be a molded or cast component, and may provide an integrally formed combination of tip (82), a ramp (90) having a ramp surface (92), and a marker engaging element (94). Ramp surface (92) may aid in directing marker (200) from internal lumen (75) through side opening (74). Marker engaging element (94) may be employed to substantially retain marker (200) in internal lumen (75) until the user intends to deploy marker (200).

Marker engaging element (94) of the present example is disposed within internal lumen (75), and at least a portion of marker engaging element (94) is disposed distally of proximal end (74A) of side opening (74). Marker engaging element (94) extends along a portion of the floor of lumen (75) under the opening (74); and is positioned to reinforce the portion of deployer tube (72) in which opening (74) is formed. For instance, by positioning marker engaging element (94) underneath opening (74) as shown in FIG. 8, marker engaging element (94) may help to substantially stiffen deployer tube (72) in the region where the wall of deployer tube (72) is cut to form opening (174). Marker engaging element (94) extends from the proximal-most portion of ramp surface (92), and does not extend proximally of side opening (74), though in some other versions, a portion of marker engaging element (94) could extend proximally of opening (74) if desired. Marker engaging element (94) is in the form of a step having a generally uniform thickness (T) along the element's axial length, except that marker engaging element (94) has a tapered proximal end (96) in the present example. Tapered proximal end (96) may form an included angle with the longitudinal axis of the lumen (75) (included angle with a horizontal line in FIG. 8) of about 45 degrees, while ramp surface (92) may form an included angle with the longitudinal axis of about 30 degrees. Of course, these angles are mere examples, and it should be understood that any other suitable angles may be used. As shown in FIG. 8, an upwardly facing surface (98) (surface facing opening (74)) of marker engaging element (94) extends distally from tapered proximal end (96) of marker engaging element (94) to contact ramp surface (92).

The thickness (T) of marker engaging element (94) may be greater than the wall thickness (t) of deployer tube (72). For instance, in some versions, thickness (T) is at least about twice the thickness (t). By way of example only, the thickness (T) of marker engaging element (94) may be between about 0.018 inch to about 0.040 inch; and the wall thickness (t) of deployer tube (72) may be between about 0.005 inch to about 0.008 inch. By further way of example only, the internal diameter of lumen (75) may be about 0.120 inch. Of course, any other suitable dimensions may be used for these components. It should be understood that, as with other components described herein, marker engaging element (94) may have any other suitable configuration, and may even be omitted as desired.

If desired, the marker engaging element (94), ramp (90), and/or tip (82) may be formed of, or include, a material that is relatively more radiopaque than the wall of deployer tube (72). For instance, where marker engaging element (94), ramp (90), and tip (82) are formed as an integral endpiece (84), endpiece (84) may include a radiopaque additive, such as barium sulfate. By way of example only, endpiece (84) may be a component molded of PEBAX, with about 20 percent by weight barium sulfate added to the molten PEBAX mold composition. The relatively more radiopaque marker engaging element (94), ramp (90), and tip (82) may be useful in distinguishing the position of those components using radiographic imaging. Also, where ramp (90) and/or step of marker engaging element (94) is/are positioned in association with opening (74), the addition of a radiopaque material may help identify the position of opening (74), and the position of the marker (200) relative to opening (74), before, during, or after deployment of marker (200).

In some versions, deployer tube (72) is generally transparent to visible light and x-ray, while endpiece (84) is generally opaque to visible light and x-ray. If desired, endpiece (84) may be colored with a dye or other suitable colorant in a liquid mold composition. For example, it may be desirable to have different size markers (e.g. length and/or diameter, etc.) for different biopsy procedures. For instance, it may be desirable to provide a larger marker if a relatively large biopsy sample is taken, and a smaller marker if a relatively small biopsy sample is taken. Endpiece (84) may be colored using one of multiple colors to indicate the size of the marker disposed in deployer tube (72). For instance, if three marker sizes are provided, endpiece (84) may be colored one of three colors to identify which of the marker sizes are disposed in the particular marker delivery device (70). Endpiece (84) may also be colored to indicate a particular size (e.g., diameter or length, etc.) or type of biopsy needle with which the marker delivery device (70) is to be used. Additionally, multiple marker delivery devices (70) may be packaged in kit form, with the kit including marker delivery devices (70) having different size markers and correspondingly colored endpieces (84). Still other variations will be apparent to those of ordinary skill in the art in view of the teachings herein.

Marker delivery device (70) may be used to deploy a marker (200) to mark a particular location within a patient. By way of example, marker delivery device (70) may be used in conjunction with any of a variety of cannulas inserted into a patient at the location to be marked. For instance, marker delivery device (70) may be used with an access cannula, as described in more detail in U.S. Non-Provisional patent application Ser. No. 12/787,492, entitled "Biopsy Marker Delivery Device," filed Jun. 6, 2010, the disclosure of which is incorporated by reference herein. See, for instance, FIGS. 8A-8B and accompanying description in U.S. Non-Provisional patent application Ser. No. 12/787,492. As another merely illustrative example, marker delivery device (70) may be used through a cannula having a lateral aperture through which a marker (200) is deployed, such as needle (12) of biopsy device (10) described previously. Marker delivery device (70) may thus be introduced to a biopsy site through a biopsy needle which can be the same needle used to collect a tissue sample from a biopsy site. While the biopsy needle through which marker delivery device (70) is used may be of the type described previously herein, it should be understood that marker delivery device (70) may be used with various other types of biopsy devices and/or various other types of instruments, components, etc.

FIG. 9 depicts marker delivery device (70) being used through biopsy needle (12) of biopsy device (10) previously described herein. It should be noted that needle (12) shown in FIG. 9 is modified from that described previously in that it lacks divider (24) (shown, for example, in FIG. 5) and therefore only includes a single lumen in which cutter (44) is positioned. Of course it should be understood that marker delivery device (70) may be used in the same manner described herein with a biopsy needle configured so as to include a divider that defines a second lumen beneath the first lumen within needle (12).

FIG. 9 shows the distal end of marker delivery device (70) extending through the lumen of cutter (44) within the cannula (14) of needle (12). It should be understood that needle (12) may be positioned in tissue, and a biopsy sample may be obtained through lateral aperture (18), as described previously. Then, after the tissue sample has been obtained and transferred proximally through needle (12), and without removing needle (12) from the patient's tissue, marker delivery device (70) may be inserted through a proximal opening in biopsy device (10) into the interior lumens of cutter (44) and biopsy needle (12). In particular, with cutter (44) in a retracted position to "open" lateral aperture (18), the distal end of deployer tube (72) is inserted into the proximal end of cutter (44) and advanced distally through cutter lumen (48) past distal edge (46) of cutter (44) into the interior lumen of needle (12) so that side opening (74) is aligned with lateral aperture (18). Since marker (200) is to be deployed through lateral aperture (18) of needle (12), cutter (44) is depicted in FIG. 9 fully retracted by cutter actuator (60) such that lateral aperture (18) is unobstructed by cutter (44). In other versions, it is contemplated that the biopsy device may be configured such that cutter (44) may be removed from the biopsy device before insertion of marker delivery device (70), such that deployer tube (72) is inserted directly into the proximal end of needle (12) and advanced distally until side opening (74) is aligned with lateral aperture (18).

As shown in FIG. 9, deployer tube (72) is advanced distally until side opening (74) of deployer tube (72) is substantially aligned both axially and circumferentially (i.e., rotationally) with lateral aperture (18) of needle (12). Then, with marker delivery device (70) and needle (12) so positioned at the biopsy site, push rod (78) may be advanced to deploy marker (200) up ramp surface (92), through side opening (74), and then through lateral aperture (18) of needle (12) into the biopsy cavity. Axial alignment of side opening (74) of marker delivery device (70) with lateral aperture (18) of biopsy needle (12) may be obtained by controlling the depth of insertion of deployer tube (72) into needle (12). By way of example, the length of marker delivery device (70) may be chosen such that axial alignment occurs when deployer tube (72) is fully inserted into needle (12). This may be accomplished, for example, by configuring deployer tube (72) and endpiece (84) such that when endpiece (84) abuts against the distal interior endwall (21) of needle (12), side opening (74) will be axially aligned with lateral aperture (18). As another merely illustrative example, a depth stop member may be positioned about deployer tube (72) near the proximal end of deployer tube (72), and such a depth stop member may restrict distal insertion of deployer tube (72) relative to needle (12) by abutting a proximal portion of the biopsy device once deployer tube has reached an insertion depth at which side opening (74) is substantially aligned axially with lateral aperture (18). Circumferential (or rotational) alignment of side opening (74) with lateral aperture (18) may be attained by rotating grip (76) of marker delivery device (70) with respect to needle (12) until proper rotational alignment is achieved.

In the depicted example, marker delivery device (70) is further configured to facilitate proper alignment of side opening (74) with the lateral aperture of a biopsy needle or other cannula with which marker delivery device (70) is used. In particular, marker delivery device (70) includes an alignment feature associated with the marker deployer tube and configured to matingly engage with a complementary alignment feature provided on a biopsy device or other cannula with which marker delivery device (70) is used. In the particular example shown in FIG. 10, alignment member (100) is configured to be matingly received by an alignment chamber on biopsy device (10). As further described herein, the alignment chamber on biopsy device (10) is provided on the body of the biopsy device (10) and is located adjacent to a port through which the deployer tube (72) of marker delivery device (70) is inserted into the interior lumen (48) of the cutter (44) and the biopsy needle (12). The alignment chamber is in communication with the interior lumen of the biopsy needle (12) such that the marker deployer tube (72) is insertable into the interior lumen of the needle (12) through the alignment chamber. The cross-sectional shape of the alignment member (100) and the corresponding alignment chamber on the biopsy device (10) are complementarily configured such that, when alignment member (100) is matingly received in the alignment chamber, the side opening (74) of the marker delivery device (70) will be in circumferential (rotational) alignment with the lateral aperture (18) of biopsy needle (12).

Figure 10:
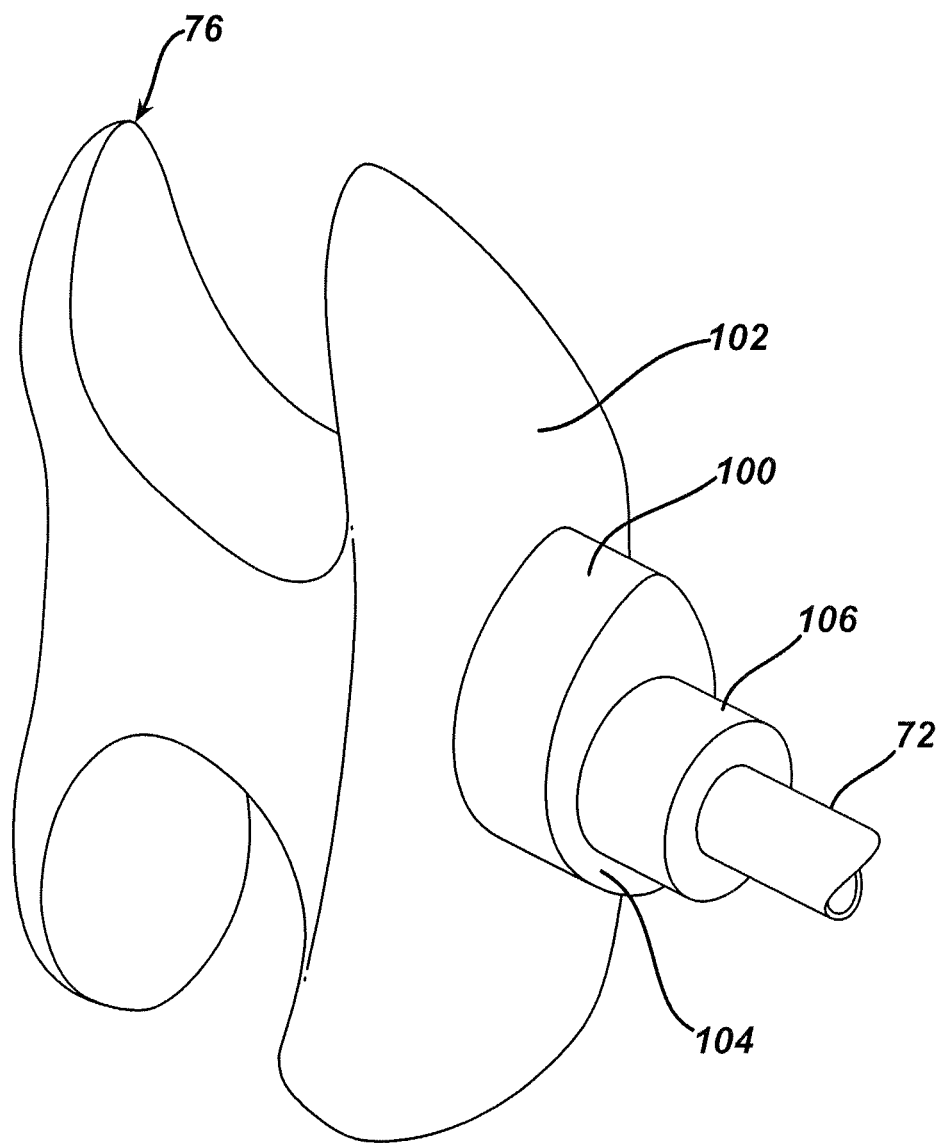
FIG. 10 depicts a perspective view of a proximal portion of the marker delivery device of FIG. 7.
Figure 11:
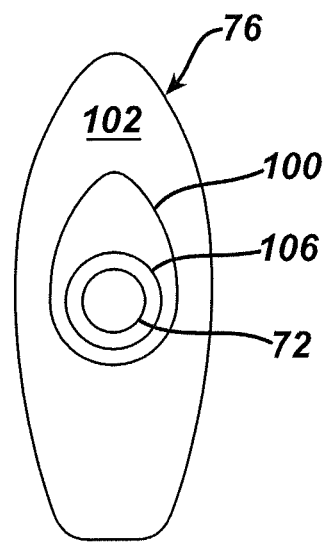
FIG. 11 depicts an end plan view of the marker delivery device of FIG. 7, viewed from the distal end of the marker delivery device toward the proximal end of the marker delivery device.

As shown in FIGS. 10-11, an alignment member (100) extends distally away from a distal end surface (102) of grip (76). In the depicted arrangement, alignment member (100) extends about the longitudinal axis of deployer tube (72), with deployer tube (72) extending through alignment member (100) into grip (76). Also in the depicted example, a cylindrical shoulder (106) extends away from distal end surface (104) of alignment member (100), and is concentric with deployer tube (72) which extends therethrough. While shoulder (106) provides additional strength and rigidity where deployer tube (72) enters grip (76), it may be omitted in alternative versions of marker delivery device (70). Grip (76), alignment member (100) and shoulder (106) may be formed from any of a variety of suitable materials. In the example shown, grip (76), alignment member (100) and shoulder (106) are unitarily molded as a single structure from a suitable medical grade plastic or other polymer. In an alternative example, grip (76), alignment member (100) and shoulder (106) are molded as two or more pieces that are joined together to form the depicted arrangement.

While cylindrical shoulder (106) in the depicted embodiment has a circular cross-section and is concentric (i.e., shares a common longitudinal axis) with deployer tube (72), alignment member (100) has a non-circular cross-section. In the particular embodiment shown, alignment member (100) has a generally tear-shaped cross-section, (as best seen in the end view of FIG. 11). As discussed below, a correspondingly-shaped alignment chamber is provided on biopsy device (10) such that when deployer tube (72) is inserted into cutter (44), alignment member (100) is matingly received in the alignment chamber so as to circumferentially align side opening (74) and lateral aperture (18) in the manner shown in FIG. 9. With respect to alignment member (100) and cylindrical shoulder (106), the cross-sectional shape described herein refers to the shape of the outer perimeter of the structure along a plane orthogonal to the longitudinal axis of deployer tube (72).

Figure 12:
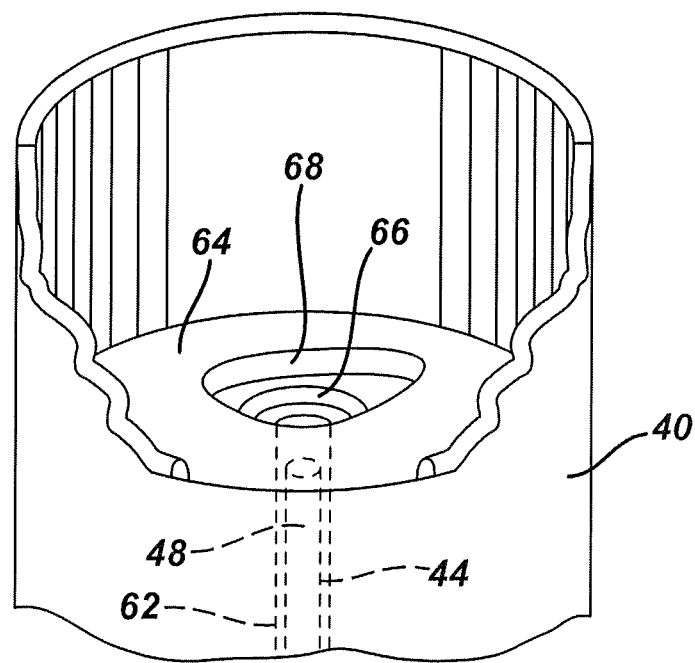
FIG. 12 depicts a partially cut-away, schematic view of the outer cup portion of the biopsy device shown in FIG. 1.

The schematic, partially cut-away illustration of FIG. 12 depicts the proximal end of body (30) of biopsy device (10), particularly the proximal end of outer cup (44). As noted previously, in order to insert deployer tube (72) of marker delivery device (70) into cutter (44) and needle (12) of biopsy device (10), cap (38) is removed along with any tissue samples and filter trays located within outer cup (44). Of course, tissue sample holder (36) may be configured such that deployer tube (72) may be inserted into cutter (44) without the need to remove a filter tray, cap (38), and/or other parts of tissue sample holder (36). In FIG. 12, cutter (44) is depicted in its fully retracted position, and is slidingly and rotatably positioned within port (62). Port (62) extends distally away from interior end wall (64) of outer cup (44), and provides communication between cutter lumen (48) and the interior volume of outer cup (44). Since cutter (44) is located at least partially within needle (12), port (62) also provides communication between the interior volume of outer cup (44) and the interior of cannula (14) of biopsy needle (12). A cylindrical bore (66) is provided in end wall (64), at the proximal end of port (62). As seen in FIG. 12, bore (66) is concentric with, and slightly larger in diameter than port (62). During use, deployer tube (72) of marker delivery device (70) is inserted into cutter (44) by inserting the distal end of deployer tube (72) into bore (66) and advancing the deployer tube (72) distally into cutter lumen (48). Bore (66) is sized and configured to receive cylindrical shoulder (106) of marker delivery device (70). Thus, since cylindrical shoulder (106) is larger in diameter than the proximal end of port (62), deployer tube (72) may be advanced distally through cutter lumen (48) until shoulder (106) advances into, and abuts against the bottom (distal end wall) of bore (66). In this manner, shoulder (106) and bore (66) assist in axially aligning side opening (74) of marker delivery device (70) and lateral aperture (18) of biopsy needle (12) (as shown in FIG. 9). In other words, shoulder (106) and bore (66) control the depth of insertion of deployer tube (72) in cutter (44) and biopsy needle (12) in order to laterally align side opening (74) with lateral aperture (18).

As also seen in the schematic illustration of FIG. 12, an alignment chamber (68) is also provided in interior end wall (64) of outer cup (40). Alignment chamber (68) is formed as a recess located adjacent to and surrounding cylindrical bore (66), such that access to bore (66), cutter lumen (48), and the interior of biopsy needle (12) is attained through alignment chamber (68). Alignment chamber (68) is similar in shape to that of alignment member (100) of marker delivery device (70). Alignment chamber (68) is also sized and configured to matingly receive alignment member (100) when deployer tube (72) is inserted through cutter lumen (48) into the distal end portion of cannula (14) of biopsy needle (12). Thus, as shown in FIG. 12, alignment chamber (68) has a generally tear-shaped cross-section (as taken on a plane orthogonal to the extended longitudinal axis of cutter lumen (48)). Alignment chamber (68) is also oriented with respect to the longitudinal axis of biopsy needle (12) such that, when alignment member (100) is matingly received therein, side opening (74) of deployer tube (72) will be circumferentially aligned with lateral aperture (18) of biopsy needle (12) (as shown in FIG. 9).

Figure 13:
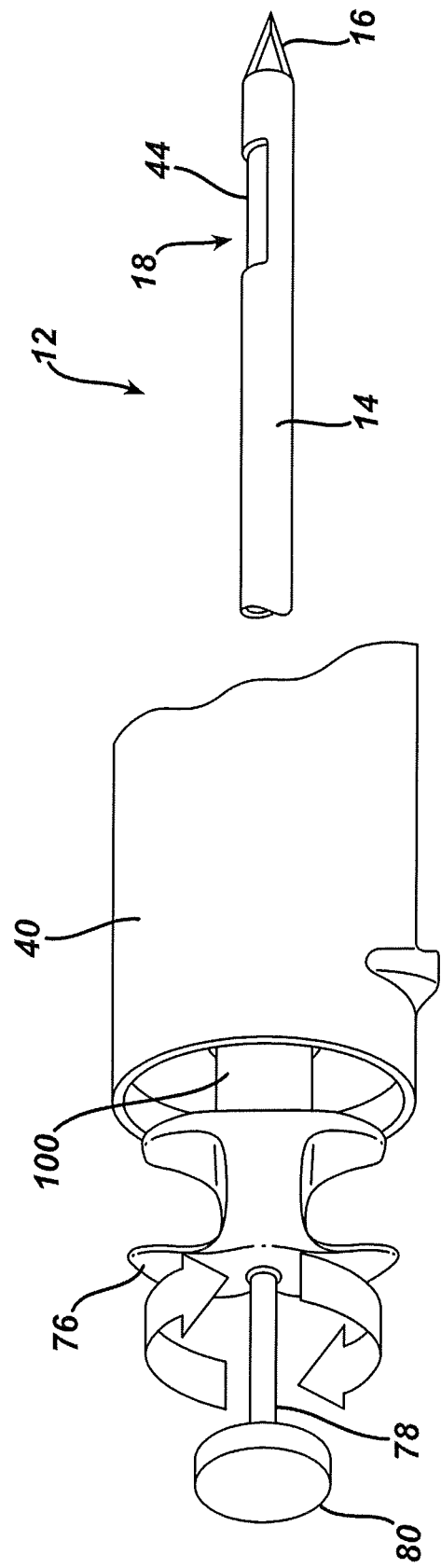
FIG. 13 depicts a schematic illustration of the marker delivery device of FIG. 7 being inserted into the biopsy device of FIG. 1, with the grip of the marker delivery device being rotated so as to align the lateral openings of the marker delivery device and the biopsy device needle.
Figure 14:
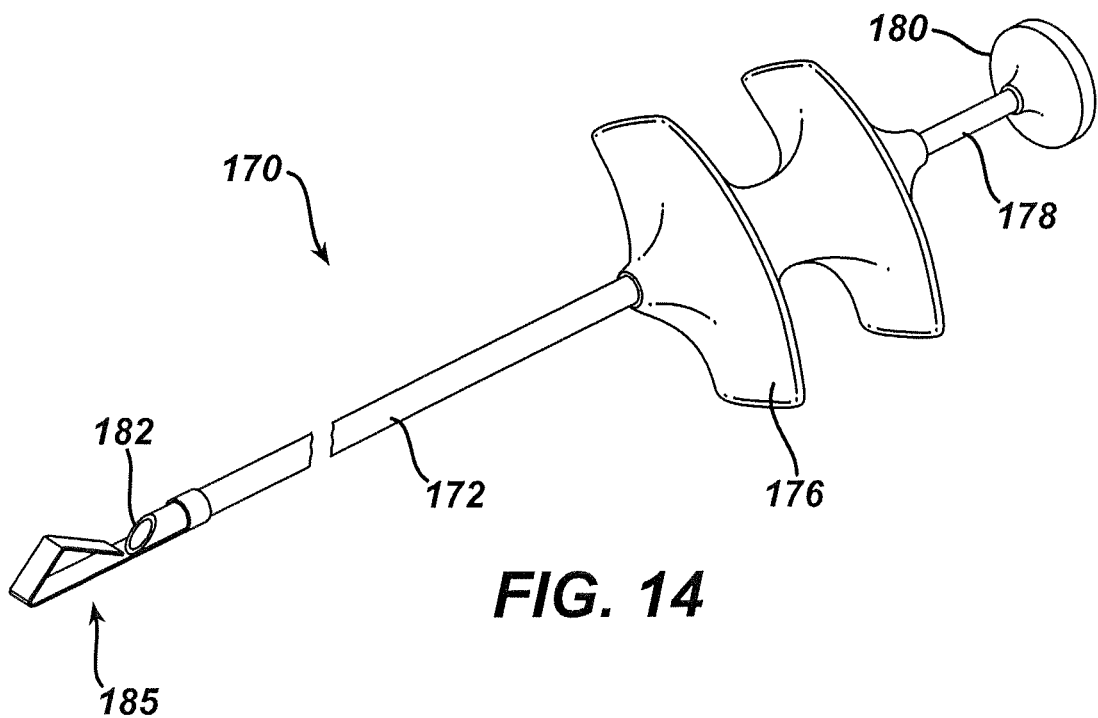
FIG. 14 depicts a perspective view of another exemplary alternative marker delivery device.

FIG. 13 schematically illustrates the manner in which alignment member (100) and corresponding alignment chamber (68) may be used to circumferentially align side opening (74) and lateral aperture (18). After cap (38) has been removed from outer cup (40) (and, in some versions, tissue samples and filter trays within outer cup (40) are also removed from outer cup (40)), the distal end of deployer tube (72) is inserted into the open end of outer cup (40) and advanced distally through alignment chamber (68) and bore (66) into cutter lumen (48) and biopsy needle (12). As deployer tube (72) is advanced further distally within cutter lumen (48), the user rotates grip (76) so as to align alignment member (100) with corresponding alignment chamber (68). When alignment member (100) is rotationally aligned with alignment chamber (68), alignment member (100) may be urged into alignment chamber (68) with cylindrical shoulder (106) being received in bore (66). Once alignment member (100) has been matingly received within alignment chamber (68), side opening (74) will be substantially aligned both axially and circumferentially. Thereafter, a marker may be deployed through lateral aperture (18) in the manner described previously. In some versions, detent features and/or other features are included to provide audible and/or tactile feedback to the user to indicate that alignment member (100) has been fully and properly received in alignment chamber (68).

The generally tear-shaped configuration of alignment member (100) and alignment chamber (68) is but merely one example of a cross-sectional shape that may be used for circumferential (i.e., rotational) alignment of the deployer tube (72) within cutter (44) and biopsy needle (12). Any of a variety of other cross-sectional shapes and configurations may be used instead. For example, alignment member (100) and alignment chamber (68) may have any of a variety of other mating cross-sectional shapes that are offset from the longitudinal axes of deployer tube (72) and biopsy needle (12), respectively. As used herein, offset simply means that the longitudinal axis of the deployer tube (72) or biopsy needle (12) does not intersect the center point of the cross-sectional shape of the alignment member (100) or alignment chamber (68), respectively. For example, tear-shaped alignment member (100) is inherently offset from the longitudinal axis of deployer tube (72), regardless of its orientation, because the tear-shaped member lacks a center point (i.e., this cross-sectional shape has a single axis of symmetry). Other single axis of symmetry cross-sectional shapes, or even asymmetrical cross-sectional shapes may be employed in the same manner. By using such shapes, there will only be a single rotational orientation of grip (76) with respect to outer cup (40) that allows alignment member (100) to be matingly received within chamber (68). Exemplary cross-sectional shapes for alignment member (100) and chamber (68) having only a single axis of symmetry include an ovoid. And any of a myriad of asymmetrical cross-sectional shapes may be employed.

Of course even cross-sectional shapes having more than one axis of symmetry may be used for alignment member (100) and chamber (68) by offsetting the alignment member and alignment chamber with respect to the longitudinal axes of the deployer tube and biopsy needle, respectively. For example, alignment member (100) and alignment chamber (68) may each have corresponding square cross-sections. Alignment member (100) may be oriented such that the center of the square cross-section (i.e., the point of intersection of the four axes of symmetry) is offset from the longitudinal axis of the deployer tube (72). Square alignment chamber (68) may be similarly offset with respect to the longitudinal axis of biopsy needle (12). In this manner, there will only be a single rotational orientation of grip (76) with respect to outer cup (40) that allows alignment member (100) to be matingly received within chamber (68).

Figure 10A:
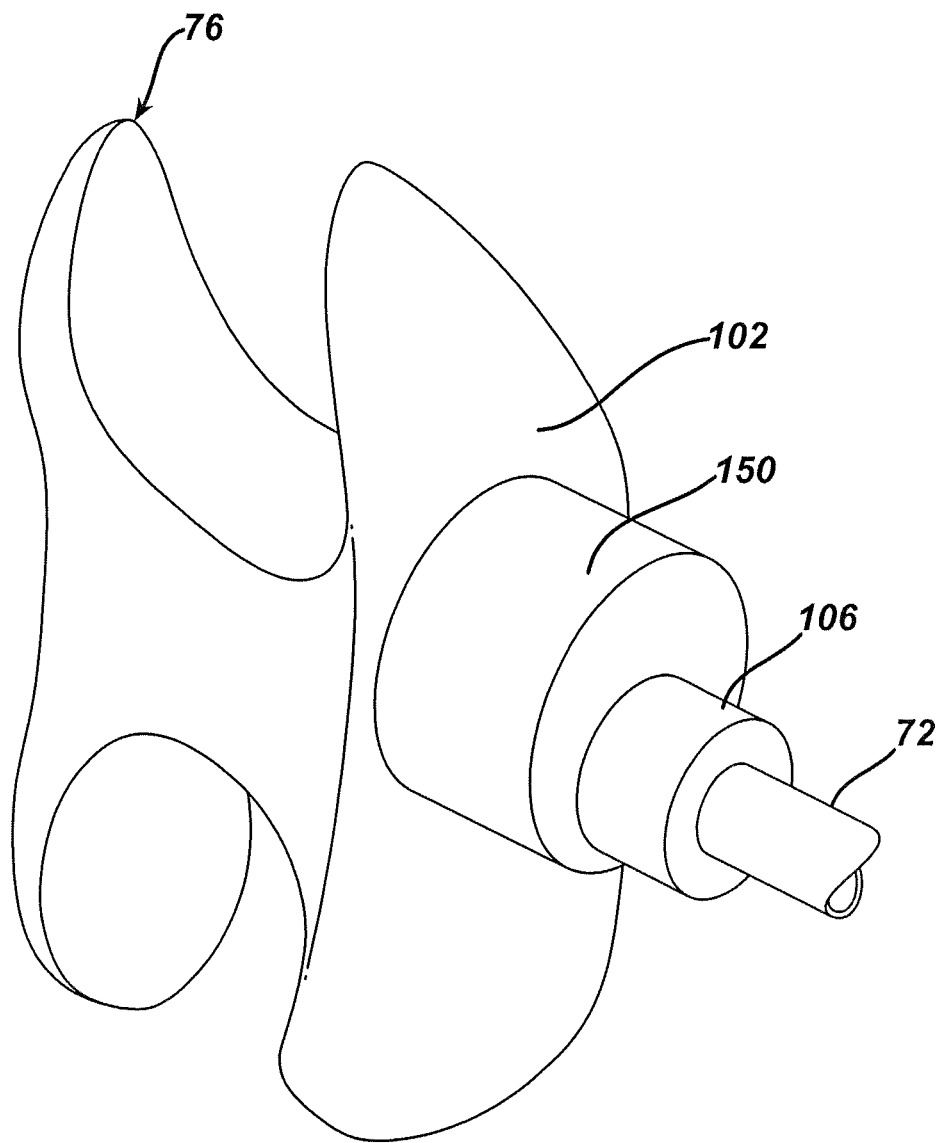
FIG. 10A depicts a proximal portion of an exemplary alternative marker delivery device having a cylindrical alignment member.

By way of further example, and as shown in FIG. 10A, alignment member (150) having a circular cross-sectional shape (i.e., a cylindrical alignment member) may be provided in place of the tear-shaped alignment member (100) described previously. In this example, the longitudinal axis (i.e., the cross-sectional center) of cylindrical alignment member (150) is offset from the longitudinal axis of deployer tube (72). A similarly shaped and oriented alignment chamber is provided on the body of biopsy device (10) in place of alignment chamber (68). Because the alignment member (150) and alignment chamber are offset from the longitudinal axes of the deployer tube and biopsy needle, respectively, there will only be a single rotational orientation of grip (76) with respect to the biopsy device that allows alignment member (150) to be matingly received within the cylindrical alignment chamber on the biopsy device.

Of course, the above examples of the alignment member and corresponding alignment chamber are merely illustrative. Other suitable configurations will be apparent to those of ordinary skill in the art in view of the teachings herein. For example, the alignment chamber may be provided at various other locations on body (30) of biopsy device (10). For instance, and as shown in U.S. Pub. No. 2008/0214955, entitled "Presentation of Biopsy Sample by Biopsy Device," cap (38) or the proximal end wall of tissue sample holder (36) may include an opening (or port) through which marker delivery device (70) may be inserted into the interior lumen of cutter (44) to deploy a marker through lateral aperture (18). An alignment chamber configured to matingly receive alignment member (100, 150) may be provided adjacent the opening in cap (38) or the proximal end wall of tissue sample holder (36) so as to surround that opening in the same manner that alignment chamber (68) is positioned relative to port (62) in FIG. 12.

As yet another exemplary alternative, a plurality of alignment members and corresponding alignment chambers may be provided in order to facilitate axial and circumferential alignment of side opening (75) and lateral aperture (18). In still another example, the positioning of the alignment member and the alignment chamber may be reversed such that the alignment member is provided on the body of the biopsy device, and the alignment chamber is provided on the marker delivery device. For example, the alignment member may extend proximally away from interior end wall (64) of outer cup (40). A corresponding alignment chamber for matingly receiving the alignment member may be provided on grip (76) of the marker delivery device, with deployer tube (72) extending out of, and distally away from the alignment chamber.

In some biopsy devices, needle (12) is rotatable relative to body (30). In some such versions, alignment chamber (68) rotates unitarily with needle (12) relative to body (30). Various suitable ways in which such unitary rotation may be provided will be apparent to those of ordinary skill in the art in view of the teachings herein.

III. Marker Delivery Device with External Marker Deployment Ramp

FIGS. 14-19 depict an exemplary alternative marker delivery device (170) that may be used to deploy one or more markers through a cannula in which the marker delivery device (170) is inserted into a patient. Marker delivery device (170) is similar to marker delivery device (70) described previously in that it includes an elongate flexible outer deployer tube (172) and a grip (176) provided at the proximal end of deployer tube (172). A push rod (178) extends coaxially in deployer tube (172). Push rod (78) is operable to translate within deployer tube (172) to deploy one or more markers contained within deployer tube (172). As with the previous example, deployer tube (172) and push rod (178) may be relatively flexible in bending so that the deployer tube (172) may be inserted along a straight or curved path to deploy a marker element at a biopsy site or other location within a patient. A plunger (180) is provided at the proximal end of rod (178) for pushing rod (178) distally in deployer tube (172) to deploy a marker out of the deployer tube (172). A user may grasp grip (176) with two fingers, and may push on plunger (180) using the thumb on the same hand, so that marker delivery device (170) may be operated by a user's single hand. Although not shown, push rod (178) may be biased proximally relative to grip (176) and deployer tube (172) by a spring or other features or structures.

If desired, one or more alignment members may be provided on grip (176) similar to that described previously herein, particularly if it is desired to use marker delivery device (170) with a biopsy device or other cannula having a corresponding alignment chamber (as described previously). In the depicted example, however, the alignment member is omitted. It should therefore be understood that the marker delivery devices (170, 270) described below may optionally have an alignment member (100, 150) or such an alignment member (100, 150) may be omitted from either or both of the marker delivery devices (170, 270) described below. Likewise, marker delivery device (70) described above may optionally have any one or more of the features of the marker delivery devices (170, 270) described below. It is therefore contemplated that the teachings herein (including those of incorporated references) may be combined in numerous permutations, such that the teachings herein should not be viewed in isolation relative to each other. Various suitable combinations of the present teachings and other variations of the present teachings will be apparent to those of ordinary skill in the art in view of the teachings herein.

One or more biopsy markers (not shown) are disposed in the internal lumen (175) of deployer tube (172), as in the previously described embodiment. The biopsy marker(s) may be similar to marker (200) described previously. By way of example, the one or more markers disposed within deployer tube (172) may comprise a biodegradable or otherwise bioresorbable body, such as a generally cylindrically shaped body of collagen or other suitable polymeric material. A metallic, generally radiopaque marker element may also be disposed within or otherwise carried by the marker body. Alternatively, the marker(s) may have any other suitable composition and/or configuration.

Deployer tube (172) may be formed of any suitable metallic or non-metallic material, or even a combination of metallic and non-metallic materials. In the present example, deployer tube (172) is formed of a relatively flexible, thin walled hollow tube formed of a suitable medical grade plastic or polymer. One suitable material is a thermoplastic elastomer, such as Polyether block amide (PEBA), such as is known under the tradename PEBAX. Deployer tube (172) may thus be formed of PEBAX, and may be substantially transparent to visible light and X-ray.

Figure 15:
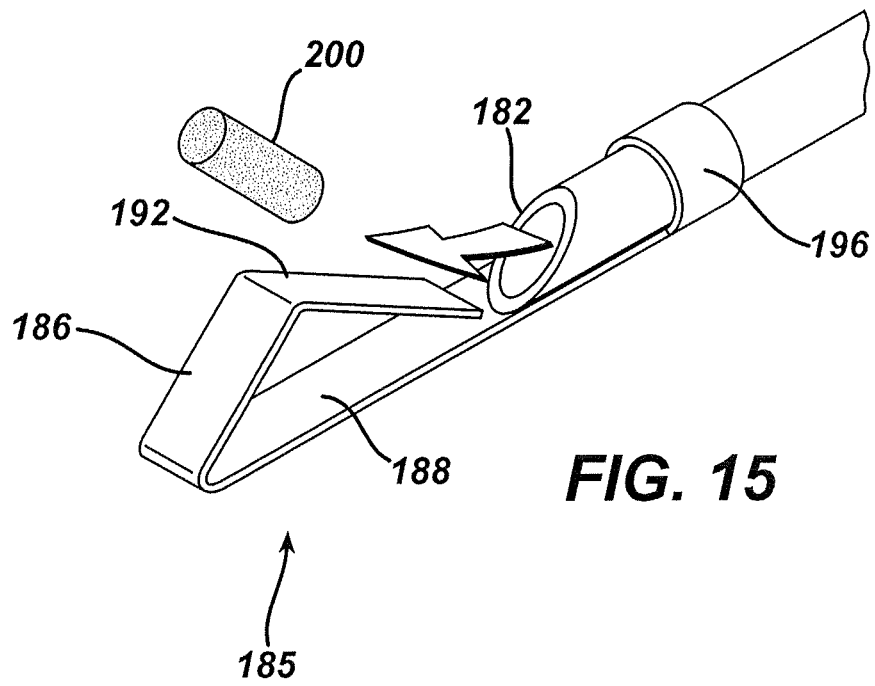
FIG. 15 depicts an enlarged perspective view of a distal portion of the marker delivery device of FIG. 14.
Figure 16:
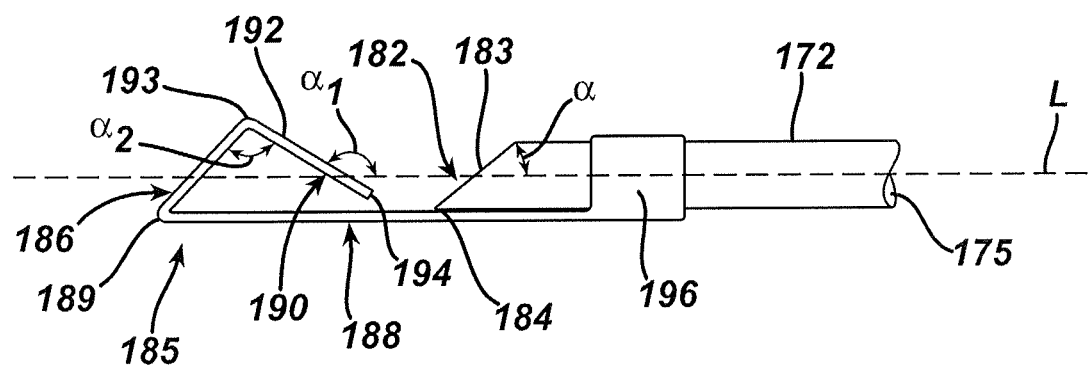
FIG. 16 depicts a side plan view of a distal portion of the marker delivery device of FIG. 14.
Figure 19:
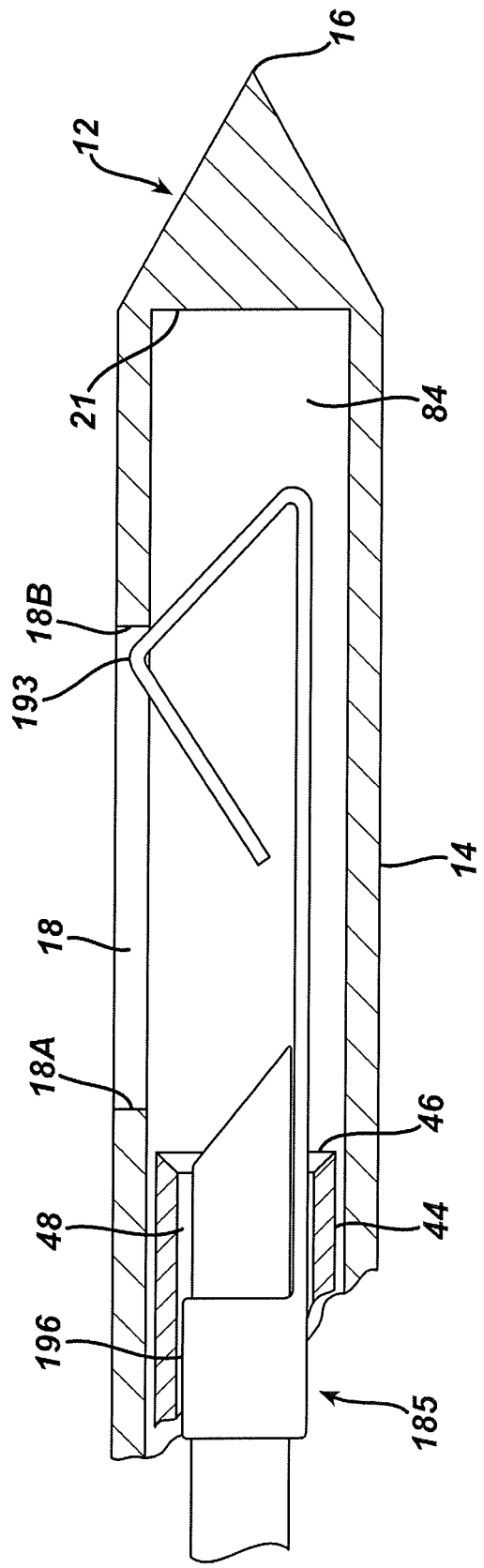
FIG. 19 depicts a side view the marker delivery device of FIG. 14 inserted in a biopsy device needle, with the biopsy device needle shown in cross-section.

In contrast to the previously described example, deployer tube (172) has an open distal end (182) (see FIG. 15). When push rod (178) is urged distally, a marker (200) is expelled from the internal lumen (175) of deployer tube (172) through open distal end (182) rather than a through a side opening provided in deployer tube (172). As best seen in FIG. 16, end surface (183) of open distal end (182) extends at an included angle to the longitudinal axis of the internal lumen (175) of deployer tube (172) which is less than 90 degrees, such that open distal end (182) is beveled. By way of example, end surface (183) may form an included angle α with the longitudinal axis L of the lumen (75) of between about 30 and about 60 degrees. In another example, end surface (183) may form an included angle α with the longitudinal axis L of the lumen (75) of about 45 degrees. When angled in this manner, end surface (183) of open distal end (182) has a distal tip (184) (see FIG. 16). Of course, these angles angle are merely examples, and it should be understood that any other suitable angles may be used. Alternatively, end surface (183) may extend perpendicular to the longitudinal axis of internal lumen (175) of deployer tube (172).

Marker delivery device (170) may be used in conjunction with any of a variety of cannulas having an open distal end. By way of example, marker delivery device (170) may be used with a biopsy device having an open ended biopsy needle rather than one having a lateral aperture (18) through which biopsy samples are acquired. Alternatively, marker delivery device (170) may be used through the open ended cannula of a trocar or other instrument. However, even when used in conjunction with the open ended cannula of a biopsy device or trocar, it still may be desirable to deploy markers at an angle to, rather than parallel to, the longitudinal axis of deployer tube (172).

In order to provide for angled (or side) deployment of a marker, marker delivery device (170) includes a ramp (190) positioned adjacent open distal end (182) of deployer tube (172). Ramp (190) has an upper surface (192) that extends distally away from open distal end (182) at an angle $\alpha_1$ to the longitudinal axis L of deployer tube (172) (see FIG. 16). By way of example, upper ramp surface (192) may extend distally away from open distal end (182) at an angle $\alpha_1$ of between about 120 and about 150 degrees with the longitudinal axis L of the lumen (75). In another example, upper ramp surface (192) may extend distally away from open distal end (182) at an angle $\alpha_1$ of about 135 degrees with the longitudinal axis L of the lumen (75). Of course, these angles are merely examples, and it should be understood that any other suitable angle may be used.

When push rod (178) is advanced distally within deployer tube (172) so as to expel a marker (200) from internal lumen (175) through open end (182), marker (200) will be urged up ramp surface (192) so as to be deployed at an angle with respect to the deployer tube (172). In this manner, marker (200) may be delivered into a site located to the side of (or lateral to) the distal end of marker delivery device (170). Thus, marker delivery device (170) provides side deployment of a marker through an open-ended cannula.

Ramp (190) may be provided adjacent open distal end (182) of deployer tube (172) in a variety of manners. In the example shown in FIGS. 14-19, ramp (190) is part of a marker guide assembly (185). Marker guide assembly (185) includes ramp (190), an upper leg (186) extending downwardly away from distal end (193) of ramp (190), a lower leg (188) extending proximally away from the distal end of upper leg (186), and a mounting sleeve (196) located at the proximal end of lower leg (188). Mounting sleeve (196) comprises a cylindrical sleeve sized and configured to be mounted over deployer tube (172) adjacent open distal end (182) of deployer tube (172), with lower leg (188) extending distally away from open distal end (182) generally parallel to longitudinal axis (L) of deployer tube (172). Mounting sleeve (196) may be attached to deployer tube (172) in any of a variety of ways such as by crimping sleeve (196) about deployer tube (172), welding, using an adhesive, or in any of a variety of ways which will be apparent to those skilled in the art in view of the teachings herein. In the example shown, mounting sleeve (196) is attached to deployer tube (172) adjacent open distal end (182) using a medically appropriate adhesive.

Upper leg (186) of marker guide assembly (185) extends between distal end (193) of ramp (190) and the distal end (189) of lower leg (188), and upper leg (186) resiliently supports ramp (190) at its distal end (193). In the example shown, upper leg (186) extends downwardly away from distal end (193) of ramp (190) at an included angle $\alpha_2$. By way of example, included angle $\alpha_2$ is between about 30 and about 60 degrees. In another example, included angle $\alpha_2$ is about 45 degrees. Of course, these angles are merely examples, and it should be understood that any other suitable angle may be used. As best seen in FIGS. 15 and 16, the proximal end (194) of ramp (190) is unattached to and spaced away from lower leg (188) of marker guide assembly (185). In addition, proximal end (194) of ramp (190) is located adjacent, and spaced away from distal tip (184) of the deployer tube (172). As further described below, such an arrangement facilitates the resilient downward deflection of ramp (190) and upper leg (186) when marker delivery device (170) is inserted into a cannula.

As shown in FIG. 18, in the depicted example ramp (190) has a height (H) defined as the distance between distal end (193) of ramp (190) and the underside of lower leg (188). This ramp height (H) is greater than the outer diameter of mounting sleeve (196) and deployer tube (172). However, when marker delivery device (170) is inserted into a cannula having an internal diameter smaller than ramp height (H), ramp (190) will be deflected downwardly such that marker delivery device (170) can be inserted into the cannula. By way of example, FIGS. 17-18 depict marker delivery device (170) being inserted into an open-ended cannula (220) for delivery of a marker to a location within a patient. While the interior diameter of cannula (220) is slightly greater than the outer diameter of mounting sleeve (196) and deployer tube (172), it is somewhat smaller than the undeflected height (H) of ramp (190). However, ramp (190) is resiliently positioned such that ramp (190) is deflected downwardly by the interior wall of cannula (220) when the distal end of marker delivery device (170) is inserted into cannula (220) and advanced distally towards open end (222) of cannula (220) (as seen in FIG. 17). In the particular example shown, the included angle between upper leg (186) and lower leg (188) is reduced and the angle ($\alpha_2$ in FIG. 16) between upper leg (186) and ramp (190) is increased as ramp (190) is deflected downwardly. In addition, free proximal end (194) of ramp (190) moves slightly downward and proximally toward distal tip (184) of deployer tube (172) as ramp (190) is deflected downwardly.

As the marker delivery device (172) is urged further distally within cannula (220) and upper distal end (193) of ramp (190) moves past open distal end (222) of cannula (220), ramp (190) will resiliently spring back to its undeflected state, as shown in FIG. 18. Since the upper distal end (193) no longer impinges against the interior wall of cannula (220), the deployer tube (172) will more freely move distally within cannula (220). This provides a tactile indication to the user that the open distal end (182) of deployer tube (172) has reached (or nearly reached) the distal end (222) of cannula (220). The return of ramp (190) to its undeflected state (e.g., as a "pop" or "snap") may also be felt by the user via grip (176), thus providing further tactile indication that the open distal end (182) of deployer tube (172) has reached (or nearly reached) the distal end (222) of cannula (220).

Figure 20:
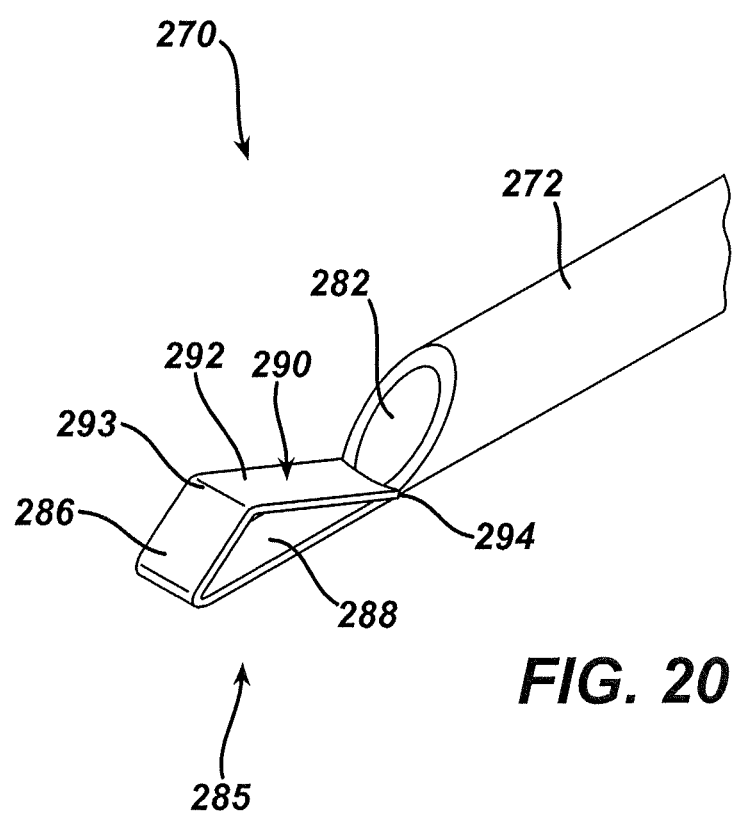
FIG. 20 depicts a perspective view of yet another exemplary alternative marker delivery device.

While marker delivery device (170) provides side deployment of a marker through an open-ended cannula, marker delivery device (170) may also be used with a closed-end biopsy device (or other closed-end cannula) having a lateral aperture. For example, and as shown in FIG. 20, marker delivery device (170) may be used in conjunction with biopsy device (10) in the same manner as marker delivery device (70) depicted in FIG. 9. Ramp surface (192) will direct an expelled marker (200) through lateral aperture (18) of biopsy needle (12). While the biopsy needle through which marker delivery device (170) is used may be of the type described previously herein, it should be understood that marker delivery device (170) may be used with various other types of biopsy devices and cannulas having a lateral aperture.

When used with biopsy device (10) or other cannula having a lateral aperture, marker delivery device (170) also provides tactile feedback to the user that that ramp (190) is properly aligned both axially and circumferentially with lateral aperture (18). In particular, the height of ramp (190) is configured such that ramp (190) is deflected resiliently downward as deployer tube (172) is urged distally through the inner lumen (48) of cutter (44) (or through the inner lumen of biopsy needle (12) when the cutter has been removed or is not present), much in the same way as depicted in FIG. 17. As the upper distal end (193) of ramp (190) travels past the distal edge (46) of cutter (44), ramp (190) will at least partially spring back toward its undeflected state. If the height of the ramp is sufficiently great, ramp (190) will not fully spring back to its uncompressed state until the upper distal end (193) of ramp (190) reaches, and is circumferentially aligned with, lateral aperture (18), as shown in FIG. 20. Thus, once the user detects that the upper distal end (193) of ramp (190) has moved past the distal edge (46) of cutter (44), the user may then simply advance deployer tube (172) distally while rotating grip (176) back in forth until the user feels ramp (190) fully spring back to its uncompressed state. Ramp (190) will return to its undeflected state as the distal end (193) of ramp (190) moves past proximal edge (18A) of lateral aperture (18). The user will then be confident that ramp (190) is properly aligned with lateral aperture (18) so that ramp (190) will direct an expelled marker through lateral aperture (18). In addition, since distal end (193) of ramp (190) protrudes upwardly into lateral aperture (18), ramp (190) will prevent the deployer tube from rotating out of proper alignment.

As also seen in FIG. 20, deployer tube (172) may be urged distally until not only ramp (190) springs back to its uncompressed state, but also upper leg (186) of marker guide assembly (185) abuts against distal edge (18B) of lateral aperture (18). This will further assist in axially aligning ramp (190) and lateral aperture (18). In the event that the user subsequently pulls deployer tube (185) proximally back through cutter (44) and needle (14), proximal edge (18A) of lateral aperture and distal edge (46) of cutter (44) may impinge against ramp (190), deflecting distal end (193) back downwardly, thereby laterally compressing marker guide assembly (185) for proximal travel through cutter lumen (48).

Marker guide assembly (185) may be formed of any suitable metallic or non-metallic material, or even a combination of metallic and non-metallic materials. In the present example, marker guide assembly (185) is formed from a relatively thin metal (e.g., stainless steel) that is stamped and then folded so as to provide ramp (190), upper leg (186), lower leg (188) and mounting sleeve (196). Alternatively, mounting sleeve (196) may be separately formed and then attached to the proximal end of lower leg (188), such as by welding. In the depicted example, the width of ramp (190), upper leg (186), and lower leg (188) is less than the outer diameter of deployer tube (172). Of course any of a variety of other materials and fabrication methods may be used to provide marker guide assembly (185).

It should also be understood that ramp (190) and marker guide assembly (185) may be provided in any of a variety of alternative configurations and constructions which will be readily apparent to those skilled in the art in view of the teachings herein. For example, FIG. 20 depicts an alternative example of a marker delivery device (270) having an open ended deployer tube (272) and a ramp (290) positioned adjacent open distal end (282) of deployer tube (272). In this example, marker guide assembly (285) includes a ramp (290), an upper leg (286), and a lower leg (288). Ramp (290) includes an upper surface (292) that extends distally away from open distal end (282) at an angle to the longitudinal axis of deployer tube (272). The angle between upper surface (292) and the longitudinal axis of deployer tube (272) is similar to that described for the previous example. Unlike the previous example, the proximal end (294) of ramp (294) is integral with the distal tip of deployer tube (272). Alternatively, proximal end (294) may be spaced away from the distal tip of deployer tube (272) in order to increase the resiliency of ramp (290) (e.g., the ability of ramp (290) to be deflected downwardly, as previously described).

Marker guide assembly (285) further includes an upper leg (286) extending downwardly away from distal end (293) of ramp (290), and a lower leg (288) extending proximally away from upper leg (286). In this example, marker guide assembly (285) is integral with the distal end (282) of deployer tube (272) rather than being provided as a separate assembly attached to the deployer tube. Marker guide assembly (285) may be formed in a variety of manners such as by integrally molding guide assembly (285) with deployer tube (272), or by stamping, folding or coining the distal end of deployer tube (272). Various other ways in which marker guide assembly (285) may be made and/or configured will be apparent to those of ordinary skill in the art in view of the teachings herein. Marker guide assembly (285) may be used in the same manner as marker guide assembly (185) described previously or in any other suitable fashion.

If desired, one or more of the components of marker guide assembly (185, 285) may be formed of, or include, a material that is relatively more radiopaque than the wall of deployer tube (172, 272). For instance, ramp (190, 290), upper leg (186, 286) and lower leg (188, 288) may include a radiopaque additive, such as barium sulfate. By way of example only, marker guide assembly (185, 285) may be a component molded of PEBAX, with about 20 percent by weight barium sulfate added to the molten PEBAX mold composition. The relatively more radiopaque marker guide assembly may be useful in distinguishing the position of those components using radiographic imaging.

In some versions, deployer tube (172, 272) is generally transparent to visible light and x-ray; while marker guide assembly (185, 285) is generally opaque to visible light and x-ray. If desired, marker guide assembly (185, 285) may be colored with a dye or other suitable colorant in a liquid mold composition. For example, it may be desirable to have different size markers (e.g. length and/or diameter, etc.) for different biopsy procedures. For instance, it may be desirable to provide a larger marker if a relatively large biopsy sample is taken; and a smaller marker if a relatively small biopsy sample is taken. Marker guide assembly (185, 285) may be colored using one of multiple colors to indicate the size of the marker disposed in deployer tube (172, 272). Marker guide assembly (185, 285) may also be colored to indicate a particular size (e.g., diameter or length, etc.) or type of biopsy needle with which the marker delivery device (170, 270) is to be used. Additionally, multiple marker delivery devices (170, 270) may be packaged in kit form, with the kit including marker delivery devices (170, 270) having different size markers and correspondingly colored marker guide assemblies (185, 285). Still other variations will be apparent to those of ordinary skill in the art in view of the teachings herein.

The foregoing examples are provided in the context of a biopsy marker delivery device. However, it will be apparent to those of ordinary skill in the art that the teachings herein may be readily applied in devices useful with radioisotope applications, as in PEM, BSGI, and other imaging methods that may employ a radioisotope or other radiation source in connection with imaging a biopsy procedure.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system comprising:
   (a) a biopsy device operable for taking one or more biopsy samples from a patient, the biopsy device comprising:
      (i) a body portion having an alignment chamber disposed at a proximal end of the body portion, wherein the alignment chamber is defined by an outer perimeter having a non-circular cross-section,
      (ii) a tissue sample holder comprising at least a part configured to selectively cover and uncover the alignment chamber, and
      (iii) a hollow biopsy needle extending distally from the body portion, the biopsy needle having a proximal end, a closed distal end, an interior lumen, and a lateral aperture configured to receive tissue; and
   (b) a marker delivery device comprising:
      (i) a marker deployer tube having a proximal end, a distal end, and a side opening formed in a sidewall of the marker deployer tube, and
      (ii) an alignment member associated with the marker deployer tube and configured to matingly engage with and be received by the alignment chamber on the biopsy device when the at least a part of the tissue sample holder uncovers the alignment chamber, wherein upon and during said receipt, the alignment member is non-rotatable with respect to the alignment chamber, wherein the alignment member has a non-circular cross-section that is complementary to the non-circular cross-section of the outer perimeter of the alignment chamber;
   wherein the marker deployer tube is insertable into the interior lumen of the biopsy needle such that, when the alignment chamber on the biopsy device and the alignment member on the marker delivery device matingly engage, the side opening of the marker deployer tube will be located within the biopsy needle in substantial alignment with the lateral aperture of the biopsy needle, wherein the marker deployer tube is configured to be received by the alignment chamber.

2. The biopsy system of claim 1, wherein the marker deployer tube extends distally away from the alignment member.

3. The biopsy system of claim 2, wherein the alignment chamber is in communication with the interior of the biopsy needle such that the distal end of the marker deployer tube is insertable into the interior lumen of the biopsy needle through the alignment chamber.

4. The biopsy system of claim 3, wherein the marker deployer tube extends through the alignment member of the marker delivery device.

5. The biopsy system of claim 1, wherein the alignment member has a cross-sectional shape which is offset from the longitudinal axis of the deployer tube; wherein the alignment chamber has a corresponding cross-sectional shape which is offset from the longitudinal axis of the biopsy needle.

6. The biopsy system of claim 5, wherein the alignment member and the alignment chamber have corresponding tear-shaped cross-sections.

7. The biopsy system of claim 1, further comprising at least one biopsy site marker disposed in the deployer tube.

8. A biopsy system comprising:
   (a) a biopsy device operable for taking one or more biopsy samples from a patient, the biopsy device comprising:
      (i) a body portion having a proximal alignment recess,
      (ii) at least a removable part of a tissue sample holder disposed at a proximal end of the body portion and configured to be removed from the body portion, wherein the at least a removable part of the tissue sample holder is configured to cover the proximal alignment recess when the at least a removable part of the tissue sample holder is coupled with the body portion, and wherein the at least a removable part of the tissue sample holder is configured to uncover the proximal alignment recess when the at least a removable part of the tissue sample holder is removed from the body portion, and
      (iii) a hollow biopsy needle extending distally from the body portion, the biopsy needle having a proximal end, a distal end, an interior lumen, and a lateral aperture configured to receive tissue, wherein the tissue sample holder is configured to receive tissue from the lateral aperture; and
   (b) a marker delivery device comprising:
      (i) a marker deployer tube having a longitudinal axis, proximal end, a distal end, and a side opening formed in a sidewall of the marker deployer tube, and
      (ii) an alignment feature associated with the marker deployer tube and configured to matingly engage with and be received by the alignment recess on the biopsy device;
   wherein, when the at least a removable part of the tissue sample holder is removed from the body portion, the marker deployer tube is insertable into the interior lumen of the biopsy needle such that, when the alignment recess on the biopsy device and the alignment feature on the marker delivery device matingly engage, the side opening of the marker deployer tube will be located within the biopsy needle in substantial alignment with the lateral aperture of the biopsy needle.

9. The biopsy system of claim 8, wherein the marker deployer tube extends distally away from the alignment feature.

10. The biopsy system of claim 9, wherein the alignment recess is in communication with the interior of the biopsy needle such that the distal end of the marker deployer tube is insertable into the interior lumen of the biopsy needle through the alignment recess.

11. The biopsy system of claim 10, wherein the marker deployer tube extends through the alignment feature of the marker delivery device.

12. The biopsy system of claim 8, wherein the alignment feature has a cross-sectional shape which is offset from the longitudinal axis of the deployer tube; wherein the alignment recess has a corresponding cross-sectional shape which is offset from the longitudinal axis of the biopsy needle.

13. The biopsy system of claim 12, wherein the alignment feature and the alignment recess have corresponding tear-shaped cross-sections.

14. The biopsy system of claim 8, further comprising at least one biopsy site marker disposed in the deployer tube.

15. A biopsy system comprising:
  (a) a biopsy device operable for taking one or more biopsy samples from a patient, the biopsy device comprising:
    (i) a body portion having an alignment chamber disposed at a proximal end,
    (ii) at least a part of a tissue sample holder configured to selectively be removed from the proximal end of the body portion such that the at least a part of the tissue sample holder is configured to cover the alignment chamber when coupled to the proximal end of the body portion and the at least a part of the tissue sample holder is configured to uncover the alignment chamber when removed from the proximal end of the body portion, and
    (iii) a hollow biopsy needle extending distally from the tissue sample holder, the biopsy needle having a proximal end, a distal end, an interior lumen, and a lateral aperture configured to receive tissue, wherein the tissue sample holder is configured to receive tissue from the lateral aperture; and
  (b) a marker delivery device comprising:
    (i) a marker deployer tube having a perimeter, a proximal end, a distal end, and a side opening formed in a sidewall of the marker deployer tube, and
    (ii) an alignment member having a perimeter, wherein the alignment member is associated with the marker deployer tube and configured to matingly engage with and be received by the alignment chamber on the biopsy device when the at least a part of the tissue sample holder is removed from the proximal end of the body portion, wherein the alignment member is disposed at a proximal end of the marker deployer tube, wherein the perimeter of the marker deployer tube is disposed within the perimeter of the alignment member;
  wherein the marker deployer tube is insertable into the interior lumen of the biopsy needle such that, when the alignment chamber on the biopsy device and the alignment member on the marker delivery device matingly engage, the side opening of the marker deployer tube will be located within the biopsy needle in substantial alignment with the lateral aperture of the biopsy.

16. The biopsy system of claim 15, wherein the marker deployer tube extends distally away from the alignment member.

17. The biopsy system of claim 16, wherein the alignment chamber is in communication with the interior of the biopsy needle such that the distal end of the marker deployer tube is insertable into the interior lumen of the biopsy needle through the alignment chamber.

18. The biopsy system of claim 15, wherein the alignment member has a cross-sectional shape which is offset from the longitudinal axis of the deployer tube; wherein the alignment chamber has a corresponding cross-sectional shape which is offset from the longitudinal axis of the biopsy needle.

19. The biopsy system of claim 18, wherein the alignment member and the alignment chamber have corresponding tear-shaped cross-sections.

20. The biopsy system of claim 15, further comprising at least one biopsy site marker disposed in the deployer tube.

* * * * *

UNITED STATES PATENT AND TRADEMARK OFFICE
CERTIFICATE OF CORRECTION

PATENT NO. : 8,529,465 B2  
APPLICATION NO. : 12/862816  
DATED : September 10, 2013  
INVENTOR(S) : Trevor W. V. Speeg et al.

Page 1 of 1

It is certified that error appears in the above-identified patent and that said Letters Patent is hereby corrected as shown below:

In the Claims:

Column 24, Claim 3, line 9, reads "...the interior of the..."; which should be deleted and replaced with "...the interior lumen of the..."

Column 25, Claim 10, line 2, reads "...the interior of the..."; which should be deleted and replaced with "...the interior lumen of the..."

Column 26, Claim 15, line 21, reads "...of the biopsy."; which should be deleted and replaced with "...of the biopsy needle."

Column 26, Claim 17, line 26, reads "...the interior of the..."; which should be deleted and replaced with "...the interior lumen of the..."

Signed and Sealed this  
First Day of April, 2014

Michelle K. Lee  
*Deputy Director of the United States Patent and Trademark Office*